(12) United States Patent
Hellinga et al.

(10) Patent No.: US 6,663,862 B1
(45) Date of Patent: Dec. 16, 2003

(54) REAGENTS FOR DETECTION AND PURIFICATION OF ANTIBODY FRAGMENTS

(75) Inventors: Homme W. Hellinga, Durham, NC (US); David J. Sloan, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/326,342

(22) Filed: Jun. 4, 1999

(51) Int. Cl.$^7$ ............... A01N 63/00; A61K 39/395; A61K 39/40; A61K 39/42; A61K 39/38
(52) U.S. Cl. ............... 424/133.1; 424/93.44; 424/130.1; 424/134.1; 424/141.1; 424/165.1; 424/178.1; 424/184.1; 424/237.1; 424/244.1; 435/734; 435/36; 435/69.1; 435/69.3; 436/512; 530/388.4
(58) Field of Search ............... 424/93.44, 130.1, 424/133.1, 134.1, 141.1, 165.1, 178.1, 237.1, 244.1, 184.1; 435/7.34, 36, 69.1, 69.3, 253.4, 326, 334, 340, 804, 808, 809; 436/512; 530/388.4, 861

(56) References Cited

U.S. PATENT DOCUMENTS 4,977,247 A * 12/1990 Fahnestock et al. ........ 530/387

OTHER PUBLICATIONS

Derrick et al. 1994. J. Mol. Biol. 243: 906–913.*
Derrick et al. 1992. Nature. 359:752–753.*
Eliasson et al. 1991. Molecular Immunology. 28(10): 1055–1061.*
Erntell et al. 1988. Molecular Immunology. 25(2): 121–126.*

Sloan et al. "Structure–Based Engineering of Environmentally Sensitive Flourophores for Monitoring Protein–Protein Interactions," Protein Engineering, Oxford University Press, vol. II ( No. 9) pp. 819–823, (1999).

Derrick et al., "Crystallization and Preliminary X–Ray Analysis of the Complex Between ad Mouse Fab Fragment and a Single IgG–Binding Domain from Streptococcal Protein G," J. Mol. Biol, p. 1253–1254, (1992).

Eliasson et al., "Structural and Functional Analysis of the Human IgG–Fab Receptor Activity of Streptococcal Protein G," Molecular Immunology, vol. 28 (No. 10), p. 1053–1061, (1991).

PCT International Search Report for International Application No. PCT/US00/15366.

* cited by examiner

Primary Examiner—Lynette R. F. Smith
Assistant Examiner—JaNa Hines
(74) Attorney, Agent, or Firm—Jenkins, Wilson & Taylor, P.A.

(57) ABSTRACT

An isolated B1 domain polypeptide of bacterial Protein G which binds a Fab fragment of an IgG but substantially does not bind a Fc fragment of an IgG. Methods for the detection and purification of IgG Fc antibody fragments and Fab antibody fragments using the isolated GB1 domain polypeptides are also disclosed.

30 Claims, 3 Drawing Sheets

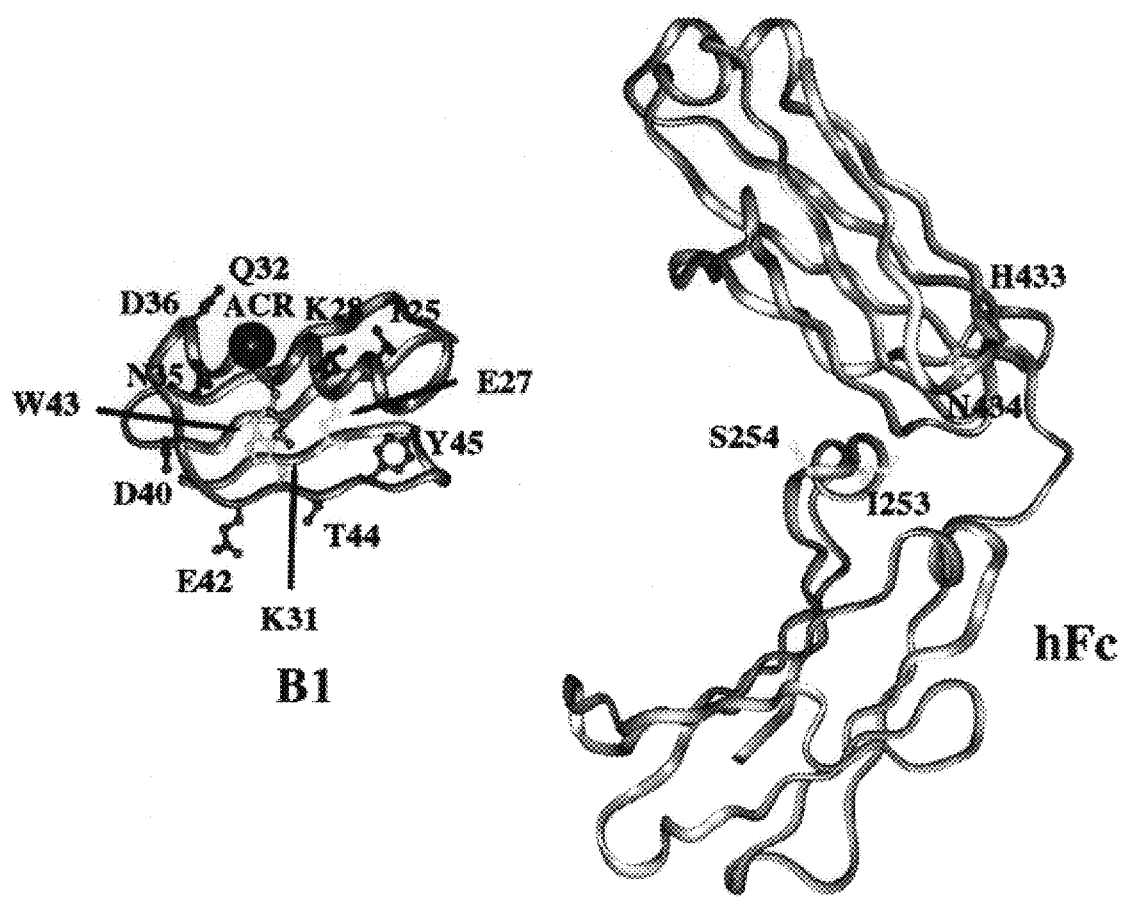
FIG. IA

SEQUENCE LISTING

<160> NUMBER OF SEQ ID NOS: 24

<210> SEQ ID NO 1
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 1

```
atg act act tac aaa tta atc ctt aat ggt aaa aca ttg aaa ggc gaa    48
Met Thr Thr Tyr Lys Leu Ile Leu Asn Gly Lys Thr Leu Lys Gly Glu
-1   1           5                  10                  15 aca act act gaa gct gtt gat gct gct act gca gaa aaa gtc ttc aaa    96
Thr Thr Thr Glu Ala Val Asp Ala Ala Thr Ala Glu Lys Val Phe Lys
                20                  25                  30 caa tac gct aac gac aac ggt gtt gac ggt gaa tgg act tac gac gat   144
Gln Tyr Ala Asn Asp Asn Gly Val Asp Gly Glu Trp Thr Tyr Asp Asp
            35                  40                  45 gcg act aag acc ttt aca gtt act gaa cat cac cat cat cac taa gct   192
Ala Thr Lys Thr Phe Thr Val Thr Glu His His His His His     Ala
        50                  55              60 tga                                                                195
```

<210> SEQ ID NO 2
<211> LENGTH: 62
<212> TYPE: PRT
<213> ORGANISM: Streptococcus sp.

<400> SEQUENCE: 2

```
Met Thr Thr Tyr Lys Leu Ile Leu Asn Gly Lys Thr Leu Lys Gly Glu
-1   1           5                  10                  15

Thr Thr Thr Glu Ala Val Asp Ala Ala Thr Ala Glu Lys Val Phe Lys
                20                  25                  30

Gln Tyr Ala Asn Asp Asn Gly Val Asp Gly Glu Trp Thr Tyr Asp Asp
            35                  40                  45

Ala Thr Lys Thr Phe Thr Val Thr Glu His His His His His
        50                  55              60
```

<210> SEQ ID NO 3
<211> LENGTH: 62
<212> TYPE: PRT
<213> ORGANISM: Streptococcus sp.

<400> SEQUENCE: 3

```
Met Thr Thr Tyr Lys Leu Ile Leu Asn Gly Lys Thr Leu Lys Gly Glu
-1   1           5                  10                  15

Thr Thr Thr Glu Ala Val Asp Ala Ala Thr Ala Glu Lys Val Phe Lys
                20                  25                  30

Cys Tyr Ala Asn Asp Asn Gly Val Asp Gly Glu Trp Thr Tyr Asp Asp
            35                  40                  45

Ala Thr Lys Thr Phe Thr Val Thr Glu His His His His
        50                  55              60
```

<210> SEQ ID NO 4
<211> LENGTH: 62
<212> TYPE: PRT
<213> ORGANISM: Streptococcus sp.

<400> SEQUENCE: 4

```
Met Thr Thr Tyr Lys Leu Ile Leu Asn Gly Lys Thr Leu Lys Gly Glu
-1   1           5                  10                  15

Thr Thr Thr Glu Ala Val Asp Ala Ala Ala Ala Glu Lys Val Phe Lys
                20                  25                  30

Gln Tyr Ala Asn Asp Asn Gly Val Asp Gly Glu Trp Thr Tyr Asp Asp
            35                  40                  45

Ala Thr Lys Thr Phe Thr Val Thr Glu His His His His
        50                  55              60
```

<210> SEQ ID NO 5
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 5

```
atg act act tac aaa tta atc ctt aat ggt aaa aca ttg aaa ggc gaa       48
Met Thr Thr Tyr Lys Leu Ile Leu Asn Gly Lys Thr Leu Lys Gly Glu
 -1   1           5                  10                  15 aca act act gaa gct gtt gat gct gct act gca gcg aaa gtc ttc aaa       96
Thr Thr Thr Glu Ala Val Asp Ala Ala Thr Ala Ala Lys Val Phe Lys
             20                  25                  30 caa tac gct aac gac aac ggt gtt gac ggt gaa tgg act tac gac gat      144
Gln Tyr Ala Asn Asp Asn Gly Val Asp Gly Glu Trp Thr Tyr Asp Asp
         35                  40                  45 gcg act aag acc ttt aca gtt act gaa cat cac cat cat cac taa gct      192
Ala Thr Lys Thr Phe Thr Val Thr Glu His His His His His     Ala
     50                  55                  60 tga                                                                  195
```

<210> SEQ ID NO 6
<211> LENGTH: 62
<212> TYPE: PRT
<213> ORGANISM: Streptococcus sp.

<400> SEQUENCE: 6

```
Met Thr Thr Tyr Lys Leu Ile Leu Asn Gly Lys Thr Leu Lys Gly Glu
 -1   1           5                  10                  15

Thr Thr Thr Glu Ala Val Asp Ala Ala Thr Ala Ala Lys Val Phe Lys
             20                  25                  30

Gln Tyr Ala Asn Asp Asn Gly Val Asp Gly Glu Trp Thr Tyr Asp Asp
         35                  40                  45

Ala Thr Lys Thr Phe Thr Val Thr Glu His His His His
     50                  55                  60
```

<210> SEQ ID NO 7
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 7

```
atg act act tac aaa tta atc ctt aat ggt aaa aca ttg aaa ggc gaa       48
Met Thr Thr Tyr Lys Leu Ile Leu Asn Gly Lys Thr Leu Lys Gly Glu
 -1   1           5                  10                  15 aca act act gaa gct gtt gat gct gct act gca gaa gcg gtc ttc aaa       96
Thr Thr Thr Glu Ala Val Asp Ala Ala Thr Ala Glu Ala Val Phe Lys
             20                  25                  30 caa tac gct aac gac aac ggt gtt gac ggt gaa tgg act tac gac gat      144
Gln Tyr Ala Asn Asp Asn Gly Val Asp Gly Glu Trp Thr Tyr Asp Asp
         35                  40                  45 gcg act aag acc ttt aca gtt act gaa cat cac cat cat cac taa gct      192
Ala Thr Lys Thr Phe Thr Val Thr Glu His His His His His     Ala
     50                  55                  60 tga                                                                  195
```

<210> SEQ ID NO 8

```
<211> LENGTH: 62
<212> TYPE: PRT
<213> ORGANISM: Streptococcus sp.

<400> SEQUENCE: 8

Met Thr Thr Tyr Lys Leu Ile Leu Asn Gly Lys Thr Leu Lys Gly Glu
 -1   1               5                  10                  15

Thr Thr Thr Glu Ala Val Asp Ala Ala Thr Ala Glu Ala Val Phe Lys
                 20                  25                  30

Gln Tyr Ala Asn Asp Asn Gly Val Asp Gly Glu Trp Thr Tyr Asp Asp
             35                  40                  45

Ala Thr Lys Thr Phe Thr Val Thr Glu His His His His His
         50                  55                  60

<210> SEQ ID NO 9
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 9 atg act act tac aaa tta atc ctt aat ggt aaa aca ttg aaa ggc gaa    48
Met Thr Thr Tyr Lys Leu Ile Leu Asn Gly Lys Thr Leu Lys Gly Glu
 -1   1               5                  10                  15 aca act act gaa gct gtt gat gct gct act gca gaa aaa gtc ttc gcg    96
Thr Thr Thr Glu Ala Val Asp Ala Ala Thr Ala Glu Lys Val Phe Ala
                 20                  25                  30 caa tac gct aac gac aac ggt gtt gac ggt gaa tgg act tac gac gat   144
Gln Tyr Ala Asn Asp Asn Gly Val Asp Gly Glu Trp Thr Tyr Asp Asp
             35                  40                  45 gcg act aag acc ttt aca gtt act gaa cat cac cat cat cac taa gct   192
Ala Thr Lys Thr Phe Thr Val Thr Glu His His His His His     Ala
         50                  55                  60 tga                                                               195

<210> SEQ ID NO 10
<211> LENGTH: 62
<212> TYPE: PRT
<213> ORGANISM: Streptococcus sp.

<400> SEQUENCE: 10

Met Thr Thr Tyr Lys Leu Ile Leu Asn Gly Lys Thr Leu Lys Gly Glu
 -1   1               5                  10                  15

Thr Thr Thr Glu Ala Val Asp Ala Ala Thr Ala Glu Lys Val Phe Ala
                 20                  25                  30

Gln Tyr Ala Asn Asp Asn Gly Val Asp Gly Glu Trp Thr Tyr Asp Asp
             35                  40                  45

Ala Thr Lys Thr Phe Thr Val Thr Glu His His His His
         50                  55                  60

<210> SEQ ID NO 11
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 11 atg act act tac aaa tta atc ctt aat ggt aaa aca ttg aaa ggc gaa    48
```

```
Met Thr Thr Tyr Lys Leu Ile Leu Asn Gly Lys Thr Leu Lys Gly Glu
-1  1           5                   10                  15 aca act act gaa gct gtt gat gct gct act gca gaa aaa gtc ttc aaa      96
Thr Thr Thr Glu Ala Val Asp Ala Ala Thr Ala Glu Lys Val Phe Lys
            20                  25                  30 caa tac gct gcg gac aac ggt gtt gac ggt gaa tgg act tac gac gat     144
Gln Tyr Ala Ala Asp Asn Gly Val Asp Gly Glu Trp Thr Tyr Asp Asp
        35                  40                  45 gcg act aag acc ttt aca gtt act gaa cat cac cat cat cac taa gct     192
Ala Thr Lys Thr Phe Thr Val Thr Glu His His His His His     Ala
        50                  55                  60 tga                                                                 195
```

<210> SEQ ID NO 12
<211> LENGTH: 62
<212> TYPE: PRT
<213> ORGANISM: Streptococcus sp.

<400> SEQUENCE: 12

```
Met Thr Thr Tyr Lys Leu Ile Leu Asn Gly Lys Thr Leu Lys Gly Glu
-1  1           5                   10                  15

Thr Thr Thr Glu Ala Val Asp Ala Ala Thr Ala Glu Lys Val Phe Lys
            20                  25                  30

Gln Tyr Ala Ala Asp Asn Gly Val Asp Gly Glu Trp Thr Tyr Asp Asp
        35                  40                  45

Ala Thr Lys Thr Phe Thr Val Thr Glu His His His His His
        50                  55                  60
```

<210> SEQ ID NO 13
<211> LENGTH: 62
<212> TYPE: PRT
<213> ORGANISM: Streptococcus sp.

<400> SEQUENCE: 13

```
Met Thr Thr Tyr Lys Leu Ile Leu Asn Gly Lys Thr Leu Lys Gly Glu
-1  1           5                   10                  15

Thr Thr Thr Glu Ala Val Asp Ala Ala Thr Ala Glu Lys Val Phe Lys
            20                  25                  30

Gln Tyr Ala Asn Asp Asn Gly Val Ala Gly Glu Trp Thr Tyr Asp Asp
        35                  40                  45

Ala Thr Lys Thr Phe Thr Val Thr Glu His His His His His
        50                  55                  60
```

<210> SEQ ID NO 14
<211> LENGTH: 62
<212> TYPE: PRT
<213> ORGANISM: Streptococcus sp.

<400> SEQUENCE: 14

```
Met Thr Thr Tyr Lys Leu Ile Leu Asn Gly Lys Thr Leu Lys Gly Glu
-1  1           5                   10                  15

Thr Thr Thr Glu Ala Val Asp Ala Ala Thr Ala Glu Lys Val Phe Lys
            20                  25                  30

Gln Tyr Ala Asn Asp Asn Gly Val Asp Gly Ala Trp Thr Tyr Asp Asp
        35                  40                  45

Ala Thr Lys Thr Phe Thr Val Thr Glu His His His His His
        50                  55                  60
```

<210> SEQ ID NO 15

-continued

```
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 15 atg act act tac aaa tta atc ctt aat ggt aaa aca ttg aaa ggc gaa         48
Met Thr Thr Tyr Lys Leu Ile Leu Asn Gly Lys Thr Leu Lys Gly Glu
-1  1               5                  10                  15 aca act act gaa gct gtt gat gct gct act gca gaa aaa gtc ttc aaa         96
Thr Thr Thr Glu Ala Val Asp Ala Ala Thr Ala Glu Lys Val Phe Lys
                20                  25                  30 caa tac gct aac gac aac ggt gtt gac ggt gaa gcg act tac gac gat        144
Gln Tyr Ala Asn Asp Asn Gly Val Asp Gly Glu Ala Thr Tyr Asp Asp
            35                  40                  45 gcg act aag acc ttt aca gtt act gaa cat cac cat cat cac taa gct        192
Ala Thr Lys Thr Phe Thr Val Thr Glu His His His His His     Ala
        50                  55                  60 tga                                                                    195

<210> SEQ ID NO 16
<211> LENGTH: 62
<212> TYPE: PRT
<213> ORGANISM: Streptococcus sp.

<400> SEQUENCE: 16

Met Thr Thr Tyr Lys Leu Ile Leu Asn Gly Lys Thr Leu Lys Gly Glu
-1  1               5                  10                  15

Thr Thr Thr Glu Ala Val Asp Ala Ala Thr Ala Glu Lys Val Phe Lys
                20                  25                  30

Gln Tyr Ala Asn Asp Asn Gly Val Asp Gly Glu Ala Thr Tyr Asp Asp
            35                  40                  45

Ala Thr Lys Thr Phe Thr Val Thr Glu His His His His His
        50                  55                  60

<210> SEQ ID NO 17
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 17 atg act act tac aaa tta atc ctt aat ggt aaa aca ttg aaa ggc gaa         48
Met Thr Thr Tyr Lys Leu Ile Leu Asn Gly Lys Thr Leu Lys Gly Glu
-1  1               5                  10                  15 aca act act gaa gct gtt gat gct gct act gca gaa aaa gtc ttc aaa         96
Thr Thr Thr Glu Ala Val Asp Ala Ala Thr Ala Glu Lys Val Phe Lys
                20                  25                  30 caa tac gct aac gac aac ggt gtt gac ggt gaa tgg gcg gcg gac gat        144
Gln Tyr Ala Asn Asp Asn Gly Val Asp Gly Glu Trp Ala Ala Asp Asp
            35                  40                  45 gcg act aag acc ttt aca gtt act gaa cat cac cat cat cac taa gct        192
Ala Thr Lys Thr Phe Thr Val Thr Glu His His His His His     Ala
        50                  55                  60 tga                                                                    195

<210> SEQ ID NO 18
<211> LENGTH: 62
```

```
<212> TYPE: PRT
<213> ORGANISM: Streptococcus sp.

<400> SEQUENCE: 18

Met Thr Thr Tyr Lys Leu Ile Leu Asn Gly Lys Thr Leu Lys Gly Glu
 -1   1               5                  10                  15

Thr Thr Thr Glu Ala Val Asp Ala Ala Thr Ala Glu Lys Val Phe Lys
                 20                  25                  30

Gln Tyr Ala Asn Asp Asn Gly Val Asp Gly Glu Trp Ala Ala Asp Asp
             35                  40                  45

Ala Thr Lys Thr Phe Thr Val Thr Glu His His His His His
         50                  55                  60

<210> SEQ ID NO 19
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 19 atg act act tac aaa tta atc ctt aat ggt aaa aca ttg aaa ggc gaa      48
Met Thr Thr Tyr Lys Leu Ile Leu Asn Gly Lys Thr Leu Lys Gly Glu
 -1   1               5                  10                  15 aca act act gaa gct gtt gat gct gct act gca gtt aaa gtc ttc aaa      96
Thr Thr Thr Glu Ala Val Asp Ala Ala Thr Ala Val Lys Val Phe Lys
                 20                  25                  30 caa tac gct aac gac aac ggt gtt gac ggt gaa tgg act tac gac gat    144
Gln Tyr Ala Asn Asp Asn Gly Val Asp Gly Glu Trp Thr Tyr Asp Asp
             35                  40                  45 gcg act aag acc ttt aca gtt act gaa cat cac cat cat cac taa gct    192
Ala Thr Lys Thr Phe Thr Val Thr Glu His His His His His     Ala
         50                  55                  60 tga                                                                 195

<210> SEQ ID NO 20
<211> LENGTH: 62
<212> TYPE: PRT
<213> ORGANISM: Streptococcus sp.

<400> SEQUENCE: 20

Met Thr Thr Tyr Lys Leu Ile Leu Asn Gly Lys Thr Leu Lys Gly Glu
 -1   1               5                  10                  15

Thr Thr Thr Glu Ala Val Asp Ala Ala Thr Ala Val Lys Val Phe Lys
                 20                  25                  30

Gln Tyr Ala Asn Asp Asn Gly Val Asp Gly Glu Trp Thr Tyr Asp Asp
             35                  40                  45

Ala Thr Lys Thr Phe Thr Val Thr Glu His His His His
         50                  55                  60

<210> SEQ ID NO 21
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 21 atg act act tac aaa tta atc ctt aat ggt aaa aca ttg aaa ggc gaa      48
Met Thr Thr Tyr Lys Leu Ile Leu Asn Gly Lys Thr Leu Lys Gly Glu
```

```
          -1    1                  5                      10                         15
         aca   act   act   gaa   gct   gtt   gat   gct   gct   act   gca   tta   aaa   gtc   ttc   aaa        96
         Thr   Thr   Thr   Glu   Ala   Val   Asp   Ala   Ala   Thr   Ala   Leu   Lys   Val   Phe   Lys
                                 20                        25                        30 caa   tac   gct   aac   gac   aac   ggt   gtt   gac   ggt   gaa   tgg   act   tac   gac   gat      144
         Gln   Tyr   Ala   Asn   Asp   Asn   Gly   Val   Asp   Gly   Glu   Trp   Thr   Tyr   Asp   Asp
                     35                        40                        45 gcg   act   aag   acc   ttt   aca   gtt   act   gaa   cat   cac   cat   cat   cac   taa   gct      192
         Ala   Thr   Lys   Thr   Phe   Thr   Val   Thr   Glu   His   His   His   His   His         Ala
                     50                        55                        60 tga                                                                                                 195
```

<210> SEQ ID NO 22
<211> LENGTH: 62
<212> TYPE: PRT
<213> ORGANISM: Streptococcus sp.

<400> SEQUENCE: 22

```
Met   Thr   Thr   Tyr   Lys   Leu   Ile   Leu   Asn   Gly   Lys   Thr   Leu   Lys   Gly   Glu
-1     1                  5                       10                         15

Thr   Thr   Thr   Glu   Ala   Val   Asp   Ala   Ala   Thr   Ala   Leu   Lys   Val   Phe   Lys
                        20                        25                        30

Gln   Tyr   Ala   Asn   Asp   Asn   Gly   Val   Asp   Gly   Glu   Trp   Thr   Tyr   Asp   Asp
            35                        40                        45

Ala   Thr   Lys   Thr   Phe   Thr   Val   Thr   Glu   His   His   His   His   His
            50                        55                        60
```

<210> SEQ ID NO 23
<211> LENGTH: 195
<212> TYPE: DNA
<213> ORGANISM: Streptococcus sp.
<220> FEATURE:
<221> NAME/KEY: CDS
<222> LOCATION: (-1)..(195)

<400> SEQUENCE: 23

```
         atg   act   act   tac   aaa   tta   atc   ctt   aat   ggt   aaa   aca   ttg   aaa   ggc   gaa       48
         Met   Thr   Thr   Tyr   Lys   Leu   Ile   Leu   Asn   Gly   Lys   Thr   Leu   Lys   Gly   Glu
         -1    1                  5                       10                         15 aca   act   act   gaa   gct   gtt   gat   gct   gct   act   gca   att   aaa   gtc   ttc   aaa       96
         Thr   Thr   Thr   Glu   Ala   Val   Asp   Ala   Ala   Thr   Ala   Ile   Lys   Val   Phe   Lys
                                 20                        25                        30 caa   tac   gct   aac   gac   aac   ggt   gtt   gac   ggt   gaa   tgg   act   tac   gac   gat      144
         Gln   Tyr   Ala   Asn   Asp   Asn   Gly   Val   Asp   Gly   Glu   Trp   Thr   Tyr   Asp   Asp
                     35                        40                        45 gcg   act   aag   acc   ttt   aca   gtt   act   gaa   cat   cac   cat   cat   cac   taa   gct      192
         Ala   Thr   Lys   Thr   Phe   Thr   Val   Thr   Glu   His   His   His   His   His         Ala
                     50                        55                        60 tga                                                                                                 195
```

<210> SEQ ID NO 24
<211> LENGTH: 62
<212> TYPE: PRT
<213> ORGANISM: Streptococcus sp.

<400> SEQUENCE: 24

```
Met   Thr   Thr   Tyr   Lys   Leu   Ile   Leu   Asn   Gly   Lys   Thr   Leu   Lys   Gly   Glu
-1     1                  5                       10                         15

Thr   Thr   Thr   Glu   Ala   Val   Asp   Ala   Ala   Thr   Ala   Ile   Lys   Val   Phe   Lys
                        20                        25                        30
```

```
                                    -continued

Gln Tyr Ala Asn Asp Asn Gly Val Asp Gly Glu Trp Thr Tyr Asp Asp
             35                  40                  45

Ala Thr Lys Thr Phe Thr Val Thr Glu His His His His His
         50                  55                  60
```

REAGENTS FOR DETECTION AND PURIFICATION OF ANTIBODY FRAGMENTS

GRANT STATEMENT

This work was supported by grant N00014-98-1-0110 from the Office of Naval Research. Thus, the United States Government has certain rights in the invention.

TECHNICAL FIELD

The present invention relates to detection and purification of antibody fragments. More particularly, the present invention relates to the detection and purification of Fc and Fab fragments of IgG's using reagents prepared from the B1 domain of bacterial protein G.

Table of Abbreviations

| | |
|---|---|
| ELISA | enzyme-linked immunosorbent assay |
| Fab | antigen binding fragment of an immunoglobulin |
| Fc | readily crystallized fragment of an immunoglobulin |
| GB1 | B1 domain of Protein G |
| HFc | readily crystallized fragment of a human immunoglobulin |
| Ig | immunoglobulin |
| IgG | immunoglobulin G |
| PCR | polymerase chain reaction |
| pfu | plaque forming units |

BACKGROUND ART

Protein-protein interactions play an essential role in many biological processes. Understanding the energetics of such interactions is of great importance because it defines the necessary concentrations of interacting partners, the rates at which these partners are capable of associating, and the relative concentrations of bound and free proteins in a solution. See Stites. W. E. (1997) *Chem. Rev.* 97:1233–1250. Well studied classes of protein-protein interactions (Jones, S. and Thornton, J. M. (1996) *Proc. Natl. Acad. Sci. USA* 93:13–20; LeConte, L. et al. (1999) *J. Mol. Biol.* 285:2177–2198) include hormone receptor binding and activation (Wells, J. A. and deVos, A. M. (1996) *Ann. Rev. Biochem.* 65:609–634), antibodies with protein antigens (Davies, D. R. and Cohen, G. H. (1996) *Proc. Natl. Acad. Sci. USA* 93:7–12), enzyme inhibitor complexes (Tsunogae, Y. et al. (1986) *J. Biochem.* 100:1637–46), and protein oligomerization (Argos, P. (1988) *Prot. Eng.* 2:101–113).

B1 is one of the domains of Protein G, a member of an important class of proteins which form IgG-binding receptors on the surface of certain staphylococcal and streptococcal strains, as described by Boyle, M. D. P. (1990) Bacterial Immunoglobulin-Binding Proteins, Academic Press, San Diego and Frick, I-M. et al. (1992) *Proc. Nati. Acad. Sci. USA* 89:8532–8536). It has been suggested that these proteins allow the pathogenic bacterium to evade the host immune response by coating the invading bacteria with host antibodies (Goward, C. R. et al. (1993) *Trends Biochem. Sci.* 18:136–140), thereby contributing significantly to the pathogenicity of these bacteria. Furthermore, protein G has found numerous applications in biotechnology as a reagent for affinity purification of antibodies (Stahl, S. et al. (1993) *Current Opinion in Immunology* 5:272–277), since it binds to IgGs of many different species and subclasses, as disclosed in Stone, G. C. et al. (1989) *J. Immunol.* 143:565–570 and in Fahnestock et al. (1990) U.S. Pat. No. 4,977,247. Further characterization of the sequence determinants that contribute to IgG binding may lead to new therapeutics for streptococcal infections and novel immunochemical reagents and thus represents a significant need in the art.

Staphylococcal Protein A competitively binds to a similar site on the Fc fragment of human IgG's as the B1 domain, involving in both cases hFc residues 252–254, 433–435, and 311, as described by Deisenhofer, J. (1981) *Biochemistry* 20:2361–2370 and Sauer-Eriksson, A. E. et al. (1995) *Structure* 3:265–278. Whereas the interactions between B1 and hFc are predominantly polar, half of the protein A interactions are polar and half are hydrophobic. These proteins present an example of two distinct folds which have evolved different structural features to achieve binding at very similar sites on the same target molecule.

The B1 domain of Protein G is a 56-residue domain that folds into a four-stranded β-sheet and one α-helix, as shown by NMR and X-ray crystallography. Despite its small size, the B1 domain has two separate IgG-binding sites on its surface, each interacting respectively with specific, independent sites on the Fab or Fc fragments of the antibody. Compared to most other protein-protein interactions, the Fc-binding site on the B1 protein is somewhat atypical. First, it is predominantly polar rather than hydrophobic in character (Stites, W. E. (1997) *Chem. Rev.* 97:1233–1250); second, the interfacial area is on the lower end of the observed range, ~700 Å$^2$ rather than the average 1200 Å$^2$ (Jones, S. and Thornton, J. M. (1996) *Proc. Nat. Acad. Sci. USA* 93:13–20); third, rather than a planar interaction surface typically observed in heterodimers, this interface is formed by a double "knobs-into-holes" interaction (Crick. F. H. C. (1952) *Nature* 170:882–883; Crick, F. H. C. (1953) *Acta Crystallographica* 6:689–697) in which a knob from the B1 protrudes into a hole in the hFc, and vice versa.

In view of the presence of these atypical elements within the Fc-binding site on the B1 domain of protein G, the characterization of the energetic contributions of each of these elements on the B1 domain for Fc fragments of IgG's represents a long-felt and significant need in the art. Indeed, the characterization of the energetic contributions of the atypical elements within the Fc-binding site on the B1 protein would facilitate the development of improved reagents and methods for detection and purification of antibody fragments, among other applications. The development of such reagents and methods thus represents an ongoing need in the art.

SUMMARY OF THE INVENTION

In accordance with the present invention, an isolated GB1 domain polypeptide which exhibits binding activity for an Fab fragment of an IgG but exhibits substantially no binding activity for an Fc fragment of an IgG is disclosed.

Preferably, the isolated GB1 domain polypeptide of the present invention further comprises a disrupted "knobs-into-holes" binding site for a Fc fragment of an IgG. More preferably still, the isolated GB1 domain polypeptide of the present invention further comprises a mutation at a "knobs-into-holes" binding site on the GB1 polypeptide for a Fc fragment of an IgG GB1 domain polypeptide, the mutation comprising an amino acid substitution.

In accordance with the present invention, a method for purifying Fc fragments of IgG's by affinity chromatography is also disclosed. The method comprising the steps of: (a) contacting a sample comprising IgG Fc and Fab fragments with a GB1 polypeptide of the present invention immobilized to a solid phase support to immobilize the IgG Fab fragments to the solid phase support; and (b) collecting the IgG Fc fragment remaining in the sample.

In accordance with the present invention, a method for purifying Fab fragments of IgG's by affinity chromatography is also disclosed. The method comprising the steps of: (a) contacting a sample comprising IgG Fc and Fab fragments with a GB1 polypeptide of the present invention immobilized to a solid phase support to immobilize the IgG Fab fragments to the solid phase support; (b) collecting the IgG Fc fragment remaining in the sample; and (c) eluting the IgG Fab fragments from the solid phase support to give purified IgG Fab fragments in the eluate.

In accordance with the present invention, a method for detecting IgG, a fragment of an IgG, or combinations thereof, in a fluid sample suspected of containing IgG, a fragment of an IgG, or combinations thereof is also disclosed. The method comprising the steps of: (a) contacting the fluid sample with a binding substance comprising the GB1 polypeptide of claim 1, under conditions favorable to binding of IgG, a fragment of an IgG, or combinations thereof to the binding substance to form a complex therebetween; and (b) detecting the complex by means of a label conjugated to the binding substance or by means of a labeled reagent that specifically binds to the complex subsequent to its formation.

It is thus an object of the present invention to provide novel reagents and methods for the detection and purification of antibody fragments.

It is another object of the present invention to novel reagents and methods for the detection and purification of antibody fragments which provides for the separation of Fc fragments and Fab fragments of an IgG, preferably an IgG of a warm-blooded vertebrate.

It is yet another object of the present invention to novel reagents and methods for the detection and purification of antibody fragments which provides for the separation of Fc fragments and Fab fragments of a human IgG.

It is still another object of the present invention to provide for the characterization of the energetic contributions of elements within the Fc-binding site on the B1 domain of protein G to binding with an Fc fragment of an IgG, preferably an IgG of a warm-blooded vertebrate.

Some of the objects of the invention having been stated hereinabove, other objects will become evident as the description proceeds, when taken in connection with the accompanying drawings and Examples as best described hereinbelow.

BRIEF DESCRIPTION OF THE DRAWINGS

FIG. 1 presents three schematic depictions of the interaction between the B1 domain and a human Fc fragment. All structures were drawn from the coordinates of the B1-hFc complex described by Sauer-Eriksson et al. (1995) *Structure* 3:265–278 and at Brookhaven accession number 1fcc.

FIG. 1A is a ribbon representation with the two partners pried apart. The residues on the surface of the B1 domain are colored according to the loss in binding free energy when mutated to alanine: yellow, >500-fold, orange, >300-fold; red, >50-fold, brown, >10-fold; grey, <2-fold. The approximate position of the reporter fluorophore covalently attached to a cysteine at position 32 is indicated by the purple sphere.

FIG. 2 presents two graphs depicting the interaction of B1 mutants with a human Fc fragment. Binding was monitored by changes in fluorescence of an acrylodan reporter group site-specifically attached to a cysteine mutation at position 32 of the B1 domain. Each point represents the average of three independent titrations, with experimental errors as indicated.

DETAILED DESCRIPTION OF THE INVENTION

Figure 1B:
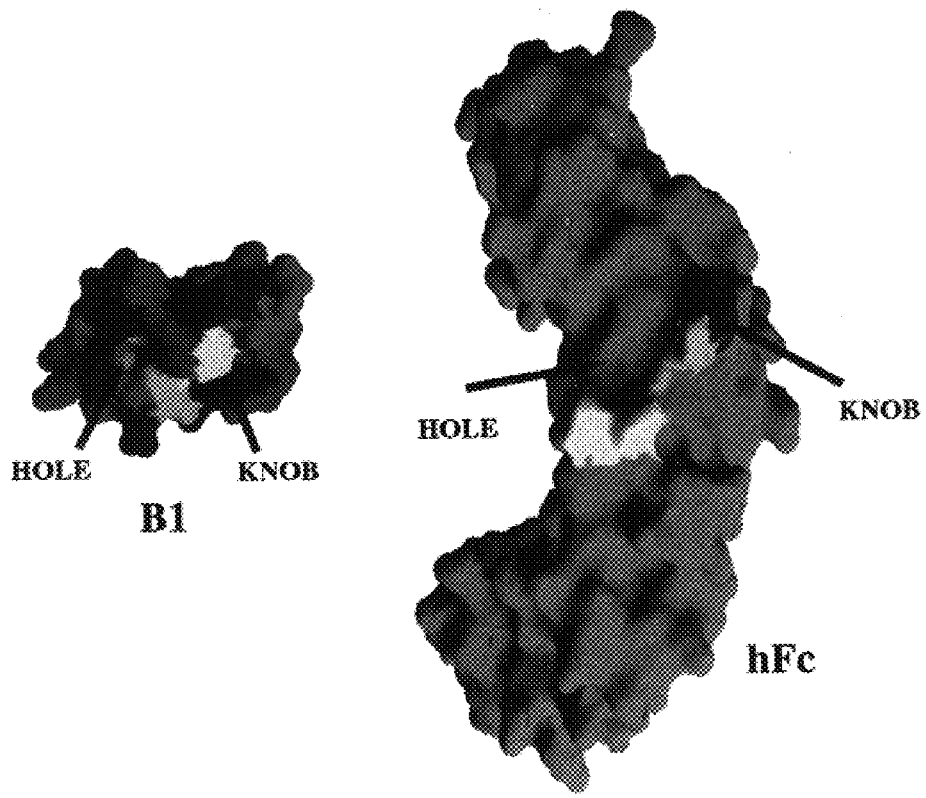
FIG. 1B is a surface rendering of the interaction, highlighting the position of the knobs and holes on the two proteins.

In accordance with the present invention, the contribution to the free energy of binding of each of the residues forming the binding site for an IgG Fc fragment on the surface of the B1 domain of protein G was determined by alanine-scanning mutagenesis. The interface between these two proteins is atypical in that it is smaller than usual, polar in character and involves two well-defined "knobs-into-holes" interactions. The bulk of the free energy of binding is contributed by three central residues which make hydrogen bonds across the interface.

Of these, the most critical interaction is formed by the glutamate 27 (Glu27) residue, which acts as a charged knob on the surface of the B1 domain, inserting into a polar hole on the Fc fragment. A single alanine mutation of this residue virtually abolishes stable complex formation. Indeed, it was observed that the substitution of the Glu 27 residue with any of the other nineteen amino acids virtually abolishes stable complex formation. Formation of a stable interface between these two proteins is therefore dominated by a small, polar "hot-spot". Thus, the detection and purification reagents and methods of the present invention in part pertain to disruption of the small, polar "hot spot".

A. General Considerations

B1 is one of the domains of Protein G, a member of an important class of proteins which form IgG-binding receptors on the surface of certain staphylococcal and streptococcal strains. See Boyle, M. D. P. (1990) *Bacterial Immunoglobulin-Binding Proteins*, Academic Press, San Diego, Calif. and Frick. I-M. et al. (1992) *Proc. Nati. Acad. Sci. USA* 89:8532–8536. The B1 domain has found numerous applications in biotechnology as a reagent for affinity purification of antibodies (Stahl, S. et al. (1993) *Current Opinion in Immunology* 5:272–277), since it binds to IgGs of many different species and subclasses as disclosed by Stone, G. C. et al. (1989) *J. Immunol.* 143:565–570.

B1 is a 56-residue domain that folds into a four-stranded D-sheet and one a-helix, as shown by NMR and X-ray crystallography. Despite its small size, the B1 domain has two separate IgG-binding sites on its surface, each interacting respectively with specific, independent sites on the Fab or Fc fragments of the antibody. The structure of a B1-Fab complex (Derrick. J. P. and Wicley, D. B. (1992) *Nature* 359:752–754 has revealed that the Fab-binding site is mediated almost entirely through backbone contacts between the edge of the β-sheet of the B1 domain and the last β-strand of the $C_H 1$ domain of the Fab fragment, thereby forming a continuous β-sheet spanning the interface between the two partners.

In contrast, a B1-Fc complex (Sauer-Eriksson, A. E. et al. (1995) *Structure* 3: 265–278) has shown that the Fc-binding site is mediated primarily by side-chain contacts between the two proteins. This is further supported by competition experiments in which an 11-residue peptide corresponding to the C-terminus of the α-helix and the N-terminal part of the third β-strand competitively inhibits binding of B1 to hFc. Frick, I-M. et al. (1992) *Proc. Natl. Acad. Sci. USA* 89:8532–8536. NMR experiments also confirm the general location of the Fc-binding site on the surface of the B1 domain (Gronenborn, A. M. and Clore, G. M. (1993) *J. Mol. Biol.* 233:331–335; Kato, K. et al. (1995) *Structure* 3:79–85). However, prior to the disclosure of the present application, the energetics of B1-Fc binding have not been characterized.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen. Antibodies, including polyclonal and monoclonal antibodies, can be prepared in accordance with a variety of art-recognized techniques, such as are exemplified in Howell et al. (1988)*Antibodies A Laboratory Manual*, (Cold Spring Harbor Laboratory Press, Cold Spring Harbor, N.Y.

Five classes of immunoglobulin have been defined in humans and the higher mammals. Those are IgG, IgM, IgA, IgD, and IgE. Additionally, humans have been found to have four subclasses of IgG and two subclasses of IgA. These immunoglobulins are present in all normal individuals and are referred to as isotypes. The type of heavy chain involved, termed gamma (γ), mu (μ), alpha (α), delta (δ), and epsilon (ε), respectively, establishes the class of immunoglobulin. Each isotype is characterized by its amino acid sequence and is the product of a different gene segment. Additionally, two types of human immunoglobulin light chain were also defined by their distinct antigenicity and named kappa (κ) and lambda (λ).

When an Ig molecule is digested by papain to yield fragments, and these digestion products are dialyzed, protein crystals accounting for one-third of the original protein mass are produced. These crystals are termed the Fc fragment (the complement binding fragment) as they constitute the "fragment crystallizable". Fc, comprising the carboxy-termini of two heavy chains, is dimeric in nature. The heavy chains are held together by inter-chain disulfide bonds. In addition, intra-chain disulfide bonds add to the conformation of the Fc region. Carbohydrates are found attached to the Fc portion of immunoglobulin.

The fragments which account for two-thirds of the original protein mass after papain digest of an Ig bind antigen in a manner equivalent to the original molecule and are termed the Fab fragments as they were antigen binding. Fab fragments are also known as monovalent fragments. It is often desirable to isolate Fab fragments from Fc fragments to study biological characteristics, such as binding characteristics, of the separate fragments. Indeed, papain digestion, yielding Fab monomers almost always generates Fc fragments and as such, the presence of Fc fragments is always an issue if the Fab monomer is the desired product of the digest. The present invention provides methods and reagents useful in isolation of the fragments and thus solves a particular problem associated with papain digestion.

Alternatively, antibody fragments may be prepared by pepsin cleavage, which releases a bivalent antigen-binding F(ab')$_2$ fragment and a complement-binding Fc' fragment. The F(ab')$_2$ fragment can be dissociated by thiol reagents into monovalent fragments. The present invention also provides methods and reagents useful in isolation of F(ab')$_2$ fragments.

The present invention particularly concerns IgG's and fragments thereof, including particularly the papain digestion fragments Fab and Fc. Thus, as used herein and in the claims, the term "IgG" is meant to refer to any IgG, including but not limited to IgG's from any warm-blooded vertebrate subject, and including but not limited to polyclonal IgG's and monoclonal IgG's. As is recognized among those having ordinary skill in the art, IgG's, including warm-blooded vertebrate IgG's, may be divided into subclasses, including but not limited to IgG1, IgG2, IgG3 and IgG4. Thus, the term "IgG" is also meant to include all subclasses of IgG's.

The recognized binding of protein G and the B1 domain of protein G with IgG's of many different species and subclasses, as disclosed in Stone, G. C. et al. (1989) *J. Immunol.* 143:565–570 coupled with the sequence modification techniques, peptide synthesis techniques, and laboratory examples disclosed herein provide adequate guidance to one of ordinary skill in the art for the detection and purification of IgG's and fragments thereof, including Fab and Fc fragments, from any warm-blooded vertebrate species using the GB1 polypeptides of the present invention in accordance with the detection and isolation methods disclosed herein.

As disclosed in detailed herein, the Fc binding segment of the GB1 polypeptide of the present invention has been modified to disrupt binding. As shown below in Table 1, mammalian Fc fragments include highly homologous structures as compared to human IgG Fc fragments, including substantially invariant residues at a binding site on the Fc fragment for a native or naturally occurring GB1 domain polypeptide. Thus, a GB1 domain polypeptide of the present invention having binding activity towards an IgG Fab fragment from a warm-blooded vertebrate, preferably a mammal, and having substantially no binding activity towards a mouse IgG Fc fragment a warm-blooded vertebrate, preferably a mammal, may be prepared using the sequence modification data and techniques, and protein synthesis techniques, disclosed herein. Therefore, a "GB1 domain polypeptide of the present invention" as used herein and in the claims is meant to encompass such a polypeptide.

Table 1 presents a compilation of a sequence alignment data for preferred IgG species and subtypes. This alignment was constructed through a blast search which was performed on the World Wide Web at: http://www.ncbi.nlm.nih.gov/BLAST/. The target sequence that was searched with was a generic eukaryotic IgG Fc sequence and these were then all aligned against a human IgG1 Fc sequence. The alignment shown in Table 1 below is of the most relevant regions of the Fc domain which contacts with the B1 domain. See also FIG. 1B. In each segment of 10 residues, it is the middle two residues (residue number 5 and 6, I and S in the first column and H and N in the second column) that are deemed to be important Fc residues for binding. It is noted that these residues are nearly invariant. The numbers shown are the amino acid number for the four important residues, the numbering convention is that from human IgG1 Fc fragment.

TABLE 1

|  | 253, 254 | 433, 434 |
|---|---|---|
| IgG k chain | ...DTLMISRTPE... | HEALHNHYTQ... |
| IgG1 human | ...DTLMISRTPE... | HEALHNHYTQ... |
| IgG2 human | ...DTLMISRTPE... | HEALHNHYTQ... |
| IgG3 human | ...DTLMISRPTE... | HEALHNRFTQ... |
| IgG4 human | ...DTLMISRTPE... | HEALHNHYTQ... |
| IgG1 mouse | ...DVLTITLTPK... | HEGLHNHHTE... |
| IgG2a mouse | ...DVLMISLSPI... | HEGLHNHHTT... |
| IgG2b mouse | ...DVLMISLTPK... | HEGLKNYYLK... |
| IgG3 mouse | ...DALMISLTPK... | HEALHNHHTQ... |
| IgG2a pig | ...DTLMISRTPQ... | HEALHNHYTQ... |
| IgG2b pig | ...DTLMISRTPQ... | HEALHNHYTQ... |
| IgG3 pig | ...DTLMISQTPE... | HEALRNHYTQ... |
| IgG4 pig | ...DTLMISRTPK... | HEALHNHYTQ... |
| IgG Rat | ...DTLMISRTPE... | HEALHNHYTQ... |
| IgG chimp | ...DTLMISRTPE... | HEALHNHYTQ... |
| IgG Macaca | ...DTLMISRTPE... | HEALHNHYTQ... |
| IgG rabbit | ...DTLMISRTPE... | HEALHNHYTQ... |
| IgG1 cat | ...DTLSISRTPE... | HEALHSHHTQ... |
| IgG2 guinea pig | ...DTLMISLTPR... | HEALHNHVTQ... |
| IgG3 cow | ...DTLTISGTPE... | HEALRNHYKE... |

Thus, the GB1 polypeptides of the present invention may be used to bind IgG's from any suitable or desirable warm-blooded vertebrate species, including mammalian and avian species. In most research or clinical applications, the more commonly used polyclonal antibodies are likely to be prepared and isolated from rabbit, goat and horse, while the more commonly used monoclonal antibodies are likely to be prepared and isolated from mouse. IgG's and fragments thereof, including Fab and Fc fragments, prepared and isolated from mouse, rat, rabbit, goat, human and horse are particularly contemplated in accordance with the present invention.

For example, Fab and Fc fragments from a mouse IgG antibody, particularly a monoclonal antibody, have been purified and separated by the inventors in accordance with the techniques described herein using a GB1 polypeptide of the present invention. Fab and Fc fragments of IgG antibodies from goat and rabbit have also been purified and isolated using a GB1 polypeptide of the present invention. Therefore, the phrases "having binding activity for an IgG Fab fragment" and "having substantially no binding activity towards an IgG Fc fragment" as used herein in connection a GB1 polypeptide of the present invention are meant to encompass such binding characteristics as applied to IgG's, and fragments thereof, from any warm-blooded vertebrate species. Preferably, these phrases are meant to encompass IgG's, and fragments thereof, from mammalian species. Preferred mammalian species include are listed in Table 1 above, and include human, mouse, pig, rat, ape, monkey, cat, guinea pig, cow, goat and horse.

B. Polypeptides

In accordance with the present invention, an isolated GB1 domain polypeptide which exhibits binding activity for an Fab fragment of an IgG but exhibits substantially no binding activity for an Fc fragment of an IgG is disclosed. The terms "bind", "binding", "binding activity" and "binding affinity" are believed to have well-understood meanings in the art. To facilitate explanation of the present invention, the terms "bind" and "binding" are meant to refer to protein-protein interactions that are recognized to play an essential role in many biological processes, such as the binding between an antibody and an antigen. Exemplary protein-protein interactions include, but are not limited to, covalent interactions between side chains, such as disulfide bridges between cysteine residues; hydrophobic interactions between side chains; and hydrogen bonding between side chains. Particularly contemplated protein-protein interactions for the present invention are the hydrogen bonds formed between a polar "hot spot" of the natural B1 domain polypeptide and the Fc fragment of an IgG.

The terms "binding activity" and "binding affinity" are meant to refer to the tendency of one protein or polypeptide to bind or not to bind to another protein or polypeptide. The energetics of protein-protein interactions are significant in "binding activity" and "binding affinity" because they define the necessary concentrations of interacting partners, the rates at which these partners are capable of associating, and the relative concentrations of bound and free proteins in a solution.

Thus, as used herein and in the claims, the terms "substantially no binding activity" or "substantially no binding affinity" refer to a substantial lack of binding or lack of interaction between two polypeptides, e.g. between the Fc fragment of an IgG and a GB1 domain polypeptide of the present invention. These terms can be further quantified from the detailed energetics data presented in the Examples with respect to binding and lack of binding between polypeptides of the present invention and Fc fragments of IgG's. Thus, for example, a dissociation constant ($K_d$) may be used to describe a GB1 polypeptide of the present invention having "substantially no binding activity" for an Fc fragment of an IgG. Indeed, preferably, an isolated GB1 domain polypeptide of the present invention which exhibits substantially no binding activity for an Fc fragment of an IgG is characterized as having a disassociation constant for a Fc fragment of an IgG of greater than about 2 mM.

More preferably, the isolated GB1 domain polypeptide of the present invention further comprises a disrupted "knobs-into-holes" binding site for a Fc fragment of an IgG. More preferably still, the isolated GB1 domain polypeptide of the present invention further comprises a mutation at a "knobs-into-holes" binding site on the GB1 polypeptide for a Fc fragment of an IgG, the mutation comprising an amino acid substitution. Optionally, the amino acid substitution comprises the substitution of a polar amino acid residue with a comparatively non-polar amino acid residue. Preferably, the Fc is an Fc fragment of an IgG of a warm-blooded vertebrate, such as mouse, rabbit, goat, horse or human. Fc fragments of a human IgG are also referred to herein as an "hFc fragment".

A preferred embodiment of a GB1 domain polypeptide of the present invention comprises a mutation at the glutamate 27 residue of a native GB1 domain polypeptide. The mutation comprises a substitution of the glutamate 27 residue with any of the other 19 amino acids, as it has been observed by the present inventors that any such substitution substantially abolishes Fc binding activity while maintaining Fab binding activity. Optionally, the substitution may comprise a comparatively non-polar amino acid residue, such as alanine, valine, leucine and isoleucine. In the case of an hFc fragment, the mutation is further characterized as a substitution of the glutamate 27 residue with a residue substantially incapable of forming a hydrogen bond with an $O_\gamma$ of a serine 254 residue of the hFc fragment. Particularly contemplated examples of such a GB1 polypeptide are disclosed in SEQ ID NO's: 6, 20, 22 and 24.

An alternative embodiment of a GB1 domain polypeptide of the present invention comprises a mutation at a lysine 28 residue of a native GB1 domain polypeptide. The mutation comprises a substitution of the lysine 28 residue with any of the other 19 amino acids, as it is contemplated by the present inventors that any such substitution substantially abolishes Fc binding activity while maintaining Fab binding activity. Optionally, the substitution may comprise a comparatively non-polar amino acid residue, such as alanine, valine, leucine and isoleucine. A particularly contemplated example of such a GB1 polypeptide is disclosed in SEQ ID NO: 8.

An alternative embodiment of a GB1 domain polypeptide of the present invention comprises a mutation at a lysine 31 residue of a native GB1 domain polypeptide. The mutation comprises a substitution of the lysine 31 residue with any of the other 19 amino acids, as it is contemplated by the present inventors that any such substitution substantially abolishes Fc binding activity while maintaining Fab binding activity. Optionally, the substitution may comprise a comparatively non-polar amino acid residue, such as alanine, valine, leucine and isoleucine. A particularly contemplated example of such a GB1 polypeptide is disclosed in SEQ ID NO:10.

An alternative embodiment of a GB1 domain polypeptide of the present invention comprises a mutation at an asparagine 35 residue of a native GB1 domain polypeptide. The mutation comprises a substitution of the asparagine 35 residue with any of the other 19 amino acids, as it is contemplated by the present inventors that any such substitution substantially abolishes Fc binding activity while maintaining Fab binding activity. Optionally, the substitution may comprise a comparatively non-polar amino acid residue, such as alanine, valine, leucine and isoleucine. A particularly contemplated example of such a GB1 polypeptide is disclosed in SEQ ID NO:12.

An alternative embodiment of a GB1 domain polypeptide of the present invention comprises a mutation at a tryptophan 43 residue of a native GB1 domain polypeptide. The mutation comprises a substitution of the tryptophan 43 residue with any of the other 19 amino acids, as it is contemplated by the present inventors that any such substitution substantially abolishes Fc binding activity while maintaining Fab binding activity. Optionally, the substitution may comprise a comparatively non-polar amino acid residue, such as alanine, valine, leucine and isoleucine. A particularly contemplated example of such a GB1 polypeptide is disclosed in SEQ ID NO:16.

An alternative embodiment of a GB1 domain polypeptide of the present invention comprises mutations at a threonine 35 residue and at a tyrosine 45 residue of a native GB1 domain polypeptide. The mutation comprises a substitution of the threonine 35 residue and tyrosine 45 residues with any of the other 19 amino acids, as it is contemplated by the present inventors that any such substitution substantially abolishes Fc binding activity while maintaining Fab binding activity. Optionally, the substitution may comprise a comparatively non-polar amino acid residue, such as alanine, valine, leucine and isoleucine. A particularly contemplated example of such a GB1 polypeptide is disclosed in SEQ ID NO:18.

Thus, as used herein and in the claims, the terms "GB1 domain protein" and "GB1 domain polypeptide" refer to polypeptides having amino acid sequences which are substantially identical to the naturally occurring or native amino acid sequences in the GB1 domain but which are altered, mutated or otherwise changed so as to exhibit Fab binding activity and substantially no Fc binding activity.

The terms "GB1 domain protein" and "GB1 domain polypeptide" also include analogs of GB1 domain molecules of the present invention which exhibit at least some biological activity in common with native GB1 domain polypeptides, that is Fab binding activity, while at the same time exhibiting substantially no Fc binding activity in accordance with the present invention. Furthermore, those skilled in the art of mutagenesis will appreciate that other analogs, as yet undisclosed or undiscovered, may be used to construct GB1 domain analogs. There is no need for a "GB1 domain protein" or "GB1 domain polypeptide" to comprise all, or substantially all of the amino acid sequence of a native GB1 domain polypeptide. Shorter or longer sequences are anticipated to be of use in the invention. Thus, these terms also include fusion or recombinant GB1 domain polypeptides and proteins. Methods of preparing such proteins are described herein in the Examples among other places.

The terms "GB1 domain-encoding nucleic acid sequence" and "GB1 domain-encoding nucleic acid segment" refer to any DNA sequence that is substantially identical to a polynucleotide sequence encoding a GB1 domain protein or GB1 domain polypeptide as defined above. The terms also refer to RNA, or antisense sequences, compatible with such DNA sequences. A "GB1 domain-encoding nucleic acid sequence" and "GB1 domain-encoding nucleic acid segment" may also comprise any combination of associated control sequences.

The term "substantially identical", when used to define either a GB1 domain polypeptide amino acid sequence, or a GB1 domain polypeptide-encoding nucleic acid sequence, means that a particular sequence, for example, a mutant sequence, varies from the sequence of a GB1 domain polypeptide of the present invention or a native GB1 domain polypeptide by one or more deletions, substitutions, or additions, the net effect of which is to retain at least some of a desired binding activity or other biological activity of the GB1 domain polypeptide. Alternatively, DNA analog sequences are "substantially identical" to specific DNA sequences disclosed herein if: (a) the DNA analog sequence is derived from coding regions of a natural GB1 domain-encoding nucleic acid molecule; or (b) the DNA analog sequence is capable of hybridization of DNA sequences of (a) under moderately stringent conditions and which encode a GB1 domain polypeptide as defined herein above; or (c) the DNA sequences are degenerative as a result of the genetic code to the DNA analog sequences defined in (a) and/or (b).

Substantially identical analog proteins preferably will be greater than about 60% identical to the corresponding sequence of a particular sequence of sequence of a GB1 domain polypeptide of the present invention disclosed herein, or of the native GB1 protein. Sequences having lesser degrees of similarity but comparable binding activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

The GB1 polypeptides of the present invention exhibiting binding activity for Fab fragments of IgG's, particularly warm-blooded vertebrate IgG's, more particularly mammalian IgG's, and even more particularly mouse, rat, goat, rabbit, human and horse IgG's. Moreover, as discussed herein above, the Fab binding domain of the GB1 domain has been characterized in the art. Thus, any Fab binding domain of the GB1 domain having Fab binding activity may be incorporated into a GB1 domain polypeptide of the present invention, including preferably the Fab binding domain of the native GB1 domain. Additionally, as described herein below, any desirable biological functional equivalent mutation, substitution, alteration or other change in the Fab binding domain of the GB1 domain is well within the skill of the art from the disclosure herein and is also contemplated to fall within the scope of the present invention.

C. Percent Similarity

Percent similarity may be determined, for example, by comparing sequence information using the GAP computer program, available from the University of Wisconsin Geneticist Computer Group. The GAP program utilizes the alignment method of Needleman et al. (1970), as revised by Smith et al. (1981). Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al. (1986), as described by Schwartz et al. (1979); (2) a penalty of 3.0 for each gap and an additional 0.01 penalty for each symbol and each gap; and (3) no penalty for end gaps. Other comparison techniques are described in the Examples.

The term "homology" describes a mathematically based comparison of sequence similarities which is used to identify genes or proteins with similar functions or motifs. Accordingly, the term "homology" is synonymous with the term "similarity" and "percent similarity" as defined above. Thus, the phrases "substantial homology" or "substantial similarity" have similar meanings.

D. Nucleic Acid Sequences

In certain embodiments, the invention concerns the use of GB1 domain polypeptides and GB1 domain polypeptide-encoding nucleic acids that include within their respective sequences a sequence which is essentially that of a GB1 domain-encoding nucleic acid, or the corresponding protein. The term "a sequence essentially as that of a GB1 domain-encoding nucleic acid" means that the sequence substantially corresponds to a portion of a GB1 domain polypeptide or GB1 domain polypeptide-encoding nucleic acid and has relatively few bases or amino acids (whether nucleic acid or protein) which are not identical to those of a GB1 domain protein or GB1 domain-encoding nucleic acid, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a GB1 domain protein or GB1 domain-encoding nucleic acid, will be sequences which are "essentially the same".

GB1 domain polypeptides and GB1 domain-encoding nucleic acids which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see Table 2).

TABLE 2

Functionally Equivalent Codons.

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic Acid | Asp | D | GAC | GAU | | | | |
| Glumatic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | ACG | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of IgG Fab fragment binding activity as well as the substantial lack of binding activity for IgG Fc fragments. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. See e.g., Wetmur & Davidson, (1968).

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a GB1 domain polypeptide refers to a DNA segment which contains GB1 domain polypeptide coding sequences, yet is isolated away from, or purified free from, total genomic DNA of a source species, such as Staphyloccocus sp. or Streptoccocus sp. Included within the term "DNA segment" are DNA segments and smaller fragments of such segments, and also recombinant vectors, including, for example, plasmids, cosmids, phages, viruses, and the like.

Similarly, a DNA segment comprising an isolated or purified GB1 domain-encoding nucleic acid refers to a DNA segment including GB1 domain coding sequences isolated substantially away from other naturally occurring polypeptide or protein encoding sequences. In this respect, the term "GB1 domain-encoding nucleic acid" is used for simplicity to refer to a functional protein, polypeptide or peptide encoding unit. "Isolated substantially away from other coding sequences" means that the nucleic acid of interest, in this case, the GB1 domain-encoding nucleic acid, forms the significant part of the coding region of the DNA segment, and that the DNA segment does not contain large portions of naturally-occurring coding DNA, such as large chromosomal fragments or other functional nucleic acids or coding regions. Of course, this refers to the DNA segment as originally isolated, and does not exclude GB1 domain-encoding nucleic acids or coding regions later added to the segment by the hand of man.

In particular embodiments, the invention concerns isolated DNA segments and recombinant vectors incorporating DNA sequences which encode a GB1 domain polypeptide that includes within its amino acid sequence an amino acid sequence selected from any of SEQ ID NO's:6, 8, 10, 12, 16, 18, 20, 22 and 24. It will also be understood that this invention is not limited to the particular nucleic acid and amino acid sequences of SEQ ID NO's: 5–12 and 15–24. Recombinant vectors and isolated DNA segments may therefore variously include the GB1 domain polypeptide-encoding region itself, include coding regions bearing selected alterations or modifications in the basic coding region, or include encoded larger polypeptides which nevertheless include GB1 domain polypeptide-encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in any of SEQ ID NO's:6, 8, 10, 12, 16, 18, 20, 22 and 24. Naturally, where the DNA segment or vector encodes a full length GB1 domain-encoding nucleic acid product, a most preferred nucleic acid sequence comprises any of those which are essentially as set forth in SEQ ID NO's: 5, 7, 9, 11, 15, 17, 19, 21 and 23, and which encode a polypeptide which binds an IgG Fab fragment but substantially does not bind an IgG Fc fragment.

The term "a sequence essentially as set forth in any of SEQ ID NO's:6, 8, 10, 12, 16, 18, 20, 22 and 24" means that the sequence substantially corresponds to a portion an amino acid sequence of any of SEQ ID NO's:6, 8, 10, 12, 16, 18, 20, 22 and 24 and has relatively few amino acids which are not identical to, or a biologically functional equivalent of, the amino acids of an amino acid sequence of any of SEQ ID NO's:6, 8, 10, 12, 16, 18, 20, 22 and 24. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of SEQ ID NO's:6, 8, 10, 12, 16, 18, 20, 22 and 24, will be sequences which comprise "a sequence essentially as set forth in any of SEQ ID NO's:6, 8, 10, 12, 16, 18, 20, 22 and 24".

In certain other embodiments, the invention concerns isolated DNA segments and recombinant vectors that include within their sequence a nucleic acid sequence essentially as set forth in any of SEQ ID NO's: 5, 7, 9, 11, 15, 17, 19, 21 and 23. The term "a sequence essentially as set forth in any of SEQ ID NO's: 5, 7, 9, 11, 15, 17, 19, 21 and 23" is used in the same sense as described above and means that the nucleic acid sequence substantially corresponds to a portion of any of SEQ ID NO's: 5, 7, 9, 11, 15, 17, 19, 21 and 23, respectively, and has relatively few codons which are not identical, or functionally equivalent, to the codons of any of SEQ ID NO's: 5, 7, 9, 11, 15, 17, 19, 21 and 23, respectively. Again, DNA segments which encode polypeptides exhibiting Fab binding activity but substantially no Fc binding activity will be most preferred. The term "functionally equivalent codon" is used herein to refer to codons that encode the same amino acid, such as the six codons for arginine or serine, and also to refer to codons that encode biologically equivalent amino acids (see Table 2).

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to a nucleic acid sequence set forth in any of SEQ ID NO's: 5, 7, 9, 11, 15, 17, 19, 21 and 23, respectively, such as about 10 nucleotides, for use as a PCR primer, for example. Alternatively, longer nucleic acid molecules may be prepared which are up to 1,000 or 500 base pairs in length, with segments of 200 being preferred in certain cases. DNA segments with total lengths of about 250, 200, 150, 100 and about 50 base pairs in length are also contemplated to be useful.

The DNA segments of the present invention encompass biologically functional equivalent GB1 domain proteins and polypeptides. Such sequences may rise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce changes in IgG Fab and IgG Fc binding activity or to test GB1 domain mutants in order to examine IgG Fab and IgG Fc binding activity at the molecular level.

If desired, one may also prepare fusion proteins and peptides, e.g., where the GB1 domain coding region is aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the GB1 domain-encoding nucleic acid, e.g., in bacterial cells, as may be obtained by isolating the 5' non-coding sequences located upstream of the coding segment, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a GB1 domain-encoding nucleic acid in its natural environment. Such promoters may include promoters isolated from bacterial, viral, eukaryotic, or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., (1989) *Molecular Cloning: A Laboratory Manual* (Cold Spring Harbor Laboratory Press, Cold Spring Harbor, N.Y.) and Ausubel et al. (1992) *Current Protocols in Molecular Biology*, (J. Wylie & Sons, New York, N.Y.), specifically incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccina virus promoter and the baculovirus promoter.

In an alternative embodiment, the present invention provides an expression vector comprising a polynucleotide that encodes a GB1 domain polypeptide exhibiting Fab binding activity but substantially no Fc binding activity, or other binding activity in accordance with the present invention. More preferably, an expression vector of the present invention comprises a polynucleotide that encodes a polypeptide comprising an amino acid residue sequence of any of SEQ ID NO's:6, 8, 10, 12, 16, 18, 20, 22 and 24, respectively. More preferably, an expression vector of the present invention comprises a polynucleotide comprising the nucleotide base sequence of any of SEQ ID NO's: 5, 7, 9, 11, 15, 17, 19, 21 and 23, respectively.

Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a GB1 domain polypeptide a GB1 domain polypeptide exhibiting Fab binding activity but substantially no Fc binding activity, or other binding activity in accordance with the present invention. SEQ ID NO's:5–12 and 15–24 set forth exemplary nucleotide and amino acid sequences. A host cell of the invention may comprise a eukaryotic host cell, such as a vertebrate cell, or more particularly, a mammalian cell.

In another aspect, a recombinant host cell of the present invention is a prokaryotic host cell. Preferably, a recombinant host cell of the invention is a bacterial cell, preferably a strain of *Escherichia coli* (*E. coli*). More preferably, a recombinant host cell comprises a polynucleotide under the transcriptional control of regulatory signals functional in the recombinant host cell, wherein the regulatory signals appropriately control expression of the GB1 domain polypeptide in a manner to enable all necessary transcriptional and post-transcriptional modification.

In yet another embodiment, the present invention contemplates a process of preparing a GB1 domain polypeptide comprising transfecting a cell with polynucleotide that encodes a GB1 domain polypeptide exhibiting Fab binding activity but substantially no Fc binding activity, or other binding activity in accordance with the present invention, to produce a transformed host cell; and maintaining the transformed host cell under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of *Escherichia coli*. Even more preferably, a polynucleotide transfected into the transformed cell comprises the nucleotide base sequence of any of SEQ ID NO's: 5, 7, 9, 11, 15, 17, 19, 21 and 23, respectively.

Any suitable known method of protein purification may be used to recover and purify the GB1 domain polypeptide from the host cells. The cells may be lysed, if necessary, using known chemical, physical, and/or enzymatic means. The polypeptides then may be purified from the cell lysate using such standard procedures as adsorption to immobilized immunoglobulin, as described by Sioquist, U.S. Pat. No. 3,850,798 (1974), ion-exchange or gel chromatography, precipitation (e.g., with ammonium sulfate), dialysis, filtration, or a combination of these methods.

As mentioned above, in connection with expression embodiments to prepare recombinant GB1 domain proteins and peptides, it is contemplated that longer DNA segments will most often be used, with DNA segments encoding the entire GB1 domain polypeptide being most preferred. However, it will be appreciated that the use of shorter DNA segments to direct the expression of GB1 domain peptides, Fab binding regions or Fc binding regions, such as may be used to test binding characteristics, also falls within the scope of the invention.

DNA segments which encode GB1 domain polypeptide segments from about 15 to about 45 amino acids in length, or more preferably, from about 10 to about 20 amino acids in length are contemplated to be particularly useful. DNA segments encoding peptides will generally have a minimum coding length in the order of about 45 to about 150, or to about 30 to about 60 nucleotides. DNA segments encoding full length proteins may have a minimum coding length on the order of about 200 nucleotides for a polypeptide essentially as set forth in any of SEQ ID NO's:6, 8, 10, 12, 16, 18, 20, 22 and 24, respectively.

Naturally, the present invention also encompasses DNA segments which are complementary, or essentially complementary, to the sequences set forth in any of SEQ ID NO's: 5, 7, 9, 11, 15, 17, 19, 21 and 23, respectively. The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of any of SEQ ID NO's: 5, 7, 9, 11, 15, 17, 19, 21 and 23, respectively, will be sequences which are, "a sequence essentially as set forth in any of SEQ ID NO's: 5, 7, 9, 11, 15, 17, 19, 21 and 23, respectively". Sequences which are essentially the same as those set forth in any of SEQ ID NO's: 5, 7, 9, 11, 15, 17, 19, 21 and 23, respectively, may also be functionally defined as sequences which are capable of hybridizing to a nucleic acid segment containing the complement of any of SEQ ID NO's: 5, 7, 9, 11, 15, 17, 19, 21 and 23, respectively, under relatively stringent conditions. Suitable relatively stringent hybridization conditions are described herein and are well known to those of skill in the art.

E. Biologically Functional Equivalents

As mentioned above, modification and changes may be made in the structure of the GB1 peptides described herein and still obtain a molecule having like or otherwise desirable characteristics. For example, certain amino acids may be substituted for other amino acids in a protein structure without appreciable loss of interactive capacity with an Fab fragment of IgG. Additionally, certain amino acids may be substituted for other amino acids in a protein structure without appreciable loss of disrupted interactive capacity with an Fc fragment of an IgG.

Since it is the interactive capacity and nature of a protein that defines that protein's biological activity, certain amino acid sequence substitutions can be made in a protein sequence (or, of course, its underlying DNA coding sequence) and nevertheless obtain a protein with like or even countervailing properties (e.g., binding v. substantially not binding). It is thus contemplated by the inventors that various changes may be made in the sequence of the GB1 domain polypeptides (or underlying DNA)without appreciable loss of their IgG Fab binding utility or their disrupted binding capacity with an Fc fragment of an IgG.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent binding or other biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in binding or other active sites, such residues may not generally be exchanged. This is the case in the present invention, where any changes, for example, in the Fab-binding site characterized by backbone contacts between the edge of the β-sheet of the B1 domain polypeptide and the last β-strand of the $C_H1$ domain of the Fab fragment, could result in a loss of an aspect of the Fab binding utility of the resulting peptide for the present invention.

Amino acid substitutions, such as those which might be employed in modifying the GB1 domain polypeptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (4.5). The amino acids having a positive hydropathic index may also be referred to as "non-polar" residues, while the amino acids having a negative hydropathic index may also be referred to as "polar" residues.

The importance of the hydropathic amino acid index in conferring interactive biological function on a protein is generally understood in the art (Kyte & Doolittle (1982), incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). The amino acids having a positive hydrophilic index may also be referred to as "polar" residues, while the amino acids having a negative hydrophilic index may also be referred to as "non-polar" residues, or as "comparatively non-polar" residues when compared to amino acids having a positive hydrophilic index.

In making changes based upon similar hydrophilicity values, the substitution of amino acids whose hydrophilicity values are within ±2 is preferred, those which are within ±1 are particularly preferred, and those within ±0.5 are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

F. Sequence Modification Techniques

Modifications to the GB1 domain polypeptides described herein may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al. (1983)). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage. A polymerase chain reaction (PCR) based site-directed mutagenesis technique is disclosed in the Examples.

In general, site-directed mutagenesis in accordance herewith is performed by first obtaining a single-stranded vector or melting apart the two strands of a double stranded vector which includes within its sequence a DNA sequence which encodes, for example, the B1 domain of protein G. An oligonucleotide primer bearing the desired mutated sequence is prepared, generally synthetically, for example by the method of Crea et al. (1978). This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

G. Peptide Synthesis Techniques

Alternatively, the GB1 domain polypeptides of the present invention may be prepared by a peptide synthesis techniques. Such techniques are contemplated for use in preparing a polypeptide of the present invention which comprises no more than about 100 amino acid residues, preferably no more than about 80 residues, and more preferably no more than about 60 residues. Synthesized peptides can be linear or cyclic.

As used herein and in the claims, a "GB1 domain polypeptide" of the present invention includes any analog, fragment or chemical derivative of a GB1 domain polypeptide having desired binding characteristics. Such a polypeptide can be subject to various changes, substitutions, insertions, and deletions where such changes provide for certain advantages in its use. In this regard, an GB1 domain polypeptide for use in a purification method of the present invention corresponds to, rather than is identical to, the sequence of a native GB1 domain polypeptide, where one or more changes are made and it retains binding activity for IgG Fab fragments and substantially no binding activity for IgG Fc fragments as disclosed herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence of a naturally occurring GB1 domain polypeptide in which one or more residues have been conservatively substituted with a functionally similar residue and which displays binding activity for IgG Fab fragments and substantially no binding activity for IgG Fc fragments as described herein. Examples of conservative substitutions include the substitution of one non-polar (hydrophobic) residue such as alanine, isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another. Such substitutions are described in detail above with respect to an isolated and purified GB1 domain polypeptide of the present invention.

The phrase "conservative substitution" also includes the use of a chemically derivatized residue in place of a non-derivatized residue provided that such polypeptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite binding activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a native GB1 domain polypeptide, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the polypeptides of this invention can be conveniently affixed to a label or solid matrix, or carrier. Labels, solid matrices and carriers that can be used with the polypeptides of this invention are described elsewhere herein.

Amino acid residue linkers are usually at least one residue and can be 40 or more residues, more often 1 to 10 residues, but do not form GB1 domain polypeptide epitopes. Typical amino acid residues used for linking are tyrosine, cysteine, lysine, glutamic and aspartic acid, or the like. In addition, a subject polypeptide can differ, unless otherwise specified, from the natural sequence of a GB1 domain polypeptide by the sequence being modified byterminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of the peptides with the peptides of the present invention include inorganic acids such as trifluoroacetic acid (TFA), hydrochloric acid (HCI), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCI and TFA salts are particularly preferred.

Suitable bases capable of forming salts with the peptides of the present invention include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al. (1969) "Solid Phase Peptide Synthesis", W. H. Freeman Co., San Francisco, Calif.; Bodanszky et al. (1976) "Peptide Synthesis", John Wiley & Sons, Second Edition; Meienhofer. J. (1983) "Hormonal Proteins and Peptides", Vol. 2, p. 46, Academic Press, New York, N.Y.; Merrifield (1969) Adv. Enzymol. 32:221–96; Fields et al. (1990) Int. J. Peptide Protein Res., 35:161–214; U.S. Pat. No. 4,244,946 for solid phase peptide synthesis, and Schroder et al. (1965) "The Peptides", Vol.1, Academic Press, New York, N.Y. for classical solution synthesis, each of which is incorporated herein by reference. Appropriate protective groups usable in such synthesis are described in the above texts and in McOmie. J. F. W. (1973) "Protective Groups in Organic Chemistry", Plenum Press, New York, N.Y., which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. a different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for cyclizing peptides is described by Zimmer et al. (1993) Peptides 1992, pp. 393–394, ESCOM Science Publishers, B. V. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

H. Detection and Precipitation Methods

Binding substances comprising the GB1 polypeptides of the present invention have selective binding activity with an IgG, a fragment of an IgG, or combinations thereof, independent of the antibody epitope (antigen recognition specificity). Such binding does not occur between the binding substance comprising the GB1 polypeptides of the present invention and other serum components. Thus, this binding specificity can be employed for detecting and/or purifying an IgG, a fragment of an IgG, or combinations thereof. The term "fragment" thus refers any fragment of an IgG, including fragments that bind the GB1 polypeptides of the present invention, such as Fab and F(ab')$_2$ fragments.

GB1 polypeptides of the present invention are prepared as described herein above. The polypeptide is then conjugated to, or labeled with, a material that will enable visualization of the presence of the GB1 polypeptide.

The GB1 domain polypeptides of the present invention can thus be used in a variety of applications to detect antibodies or antibody fragments. For example, fluoresceinated, alkaline phosphatase labeled, peroxidase labeled, or biotinylated GB1 domain polypeptides of the present invention are used in indirect cytochemical assays to detect antibody binding to cells and tissues in histological or flow cytometric assays. Particularly, the GB1 polypeptides of the present invention labeled in this manner detect the Fab portion of an antibody molecule, and such detection may be used in a variety of research or clinical contexts.

Similarly, immobilized GB1 polypeptides of the present invention can be used to precipitate immune complexes in radioimmune and other quantitative immune or antigen capture assays. Such immunoprecipitation assays where immune complexes of radiolabeled antigens are captured on immobilized GB1 polypeptides of the present invention have wide application in the art.

By way of elaboration, the GB1 polypeptides of the present invention are used to detect the presence of IgG antibodies fragments thereof, in solutions, or on surfaces exposed to IgG antibodies, or fragments thereof, by a variety of techniques. Techniques which are used include: enzyme-linked immunosorbent assay (ELISA), radioimmunoassay (RIA), immunoblot analysis, immunofluorescent assay (IFA), immunohistochemistry, immunoelectron microscopy (IEM), and immunoilluminescence. Each technique utilizes conjugates including the GB1 polypeptides of the present invention to visualize the binding of the conjugate to IgG antibody molecules or fragments thereof.

Commonly used conjugates include, but are not limited to, enzymes such as biotin, horseradish peroxidase, alkaline phosphatase (O'Sullivan et al. (1978) FEBS Letters 95:311), acid phosphatase, beta-galactosidase (Ishikawa et al. (1978) *Scand. J. Immunol.* 8:43) and luciferase; radioisotopes such as $^{125}$I, $^{35}$S, $^{14}$C, and $^{3}$H; fluorescent dyes such as fluorescein, rhodamine, dichlorotriazinylaminofluorescein (DTAF; Blakeslee et al., *J. Immunol. Meth.* 13:320 (1977)), ferritin (Carlsson et al. (1978) *Biochem. J.* 173:723), fluoroscene isothiocyanste (FITC; McKinney et al. (1966) *Anal. Biochem.* 14:421), sulforhodamine 101 acid chloride (Texas Red) and tetra-methyrhodamine isothiocyanate (TRITC; Amante et al., *J. Immunol. Meth.*, 1:289 (1972)); colloidal gold particles (Horisberger et al., *Histochem.* 82:219 (1985)); and the like. Effective procedures for such conjugations are generally conventional, as described by Harlow et al., 1988, *Antibodies: a laboratory manual*, Cold Spring Harbor Laboratory, Cold Spring Harbor, N.Y.

The protein conjugate is stored in appropriate buffers until needed. Colloidal gold conjugates may be maintained in Tris-based stabilizing buffer, such as those described in Robinson et al., (1984) *Infect. Immun.* 46:361–366. For other conjugates, the buffer would typically be phosphate-buffered saline, pH 7.2 (PBS). However, physiological buffers such as Tris- or borate-buffered saline (TBS or BBS) in pH ranging from 6.5 to 8.0, or non-saline buffers such as acetates, bicarbonates, or citrates within this pH range may be utilized.

When needed to detect the presence of IgG antibodies or fragments thereof in a preparation, the GB1 polypeptide conjugate may be first diluted in an appropriate buffer. The extent of dilution varies according to the conjugate and sensitivity required, and is normally determined empirically for a given conjugate preparation and detection method. Dilutions typically range from 1:10 to 1:10,000. After dilution the conjugate is incubated with a sample suspected of containing IgG antibodies or fragments thereof. The incubation should proceed for about 15–60 minutes at room temperature, or about 4–16 hours at about 4° C., during which time from one to ten (optimally) GB1 polypeptide molecules will bind to any IgG antibodies or fragments thereof present. Following incubation, the sample is washed twice for about 5–10 minutes each with dilution buffer or with buffer which is compatible with the visualization conditions (if different). The presence of bound GB1 polypeptide may then be detected or visualized by chromogenic assay, radioactivity, illuminescence, fluorescence, flow cytometry or electron density, as appropriate for the conjugate.

Thus, a method for detecting IgG, a fragment of an IgG, or combinations thereof, in a sample suspected of containing IgG, a fragment of an IgG, or combinations thereof, is provided in accordance with the present invention. The method comprising the steps of: (a) contacting the sample with a binding substance comprising the GB1 polypeptide of the present invention under conditions favorable to binding of IgG, a fragment of an IgG, or combinations thereof, to the binding substance to form a complex therebetween; and (b) detecting the complex by means of a label conjugated to the binding substance or by means of a labeled reagent that specifically binds to the complex subsequent to its formation.

In the detection method of the present invention, the binding substance can be immobilized on a solid substrate. In such case, the detecting step (b) comprises: (i) contacting the complex with a reagent conjugated with a detectable label wherein the reagent specifically binds to IgG, a fragment of an IgG, or combinations thereof, and (ii) detecting the detectable label.

In the detection method of the present invention, the binding substance can be conjugated with a detectable label. In such case, the detecting step (b) comprises: (i) separating the complex from unbound labeled binding substance; and (ii) detecting the detectable label which is present in the complex or which is unbound.

The detection method of the present invention can further comprise: (i) contacting the complex with a reagent immobilized on a solid substrate to form immobilized complex thereon wherein the reagent binds to IgG, a fragment of an IgG, or combinations thereof, present in the complexes; and (ii) separating the immobilized complex from the remaining mixture.

I. Purification of IgG's and IgG Fragments

The immobilized GB1 domain polypeptides of the present invention may be used to separate or bind IgG's or fragments thereof. In particular, the immobilized GB1 domain polypeptides of the present invention bind Fab and F(ab')$_2$ fragments of IgG's and substantially do not bind Fc fragments of IgG's. Therefore, the immobilized GB1 polypeptides are particularly useful for the separation of IgG Fc fragments from IgG Fab fragments.

Conjugates of GB1 proteins may thus used to purify IgG's, a fragment of an IgG, or combinations thereof by methods similar to those used for purification of IgG antibodies with protein A. Such affinity purification methods generally utilize insoluble or immobile protein conjugates to facilitate eventual separation of the antibody and the immunoglobulin-binding protein and to separate antibody fragments. A purification procedure for IgG, a fragment of an IgG, or combinations thereof, uses a GB1 polypeptide of the present invention conjugated to an insoluble matrix by methods such as those described previously by Harlow et al. (1988) *Antibodies: a laboratory manual.* Cold Spring Harbor Laboratory, Cold Spring Harbor, N.Y. Appropriate matrices may include but are not limited to agarose, latex, magnetic or polyacrylamide beads, silica or polystyrene.

Following conjugation, any available sites on the matrix are blocked by appropriate reagents, and the conjugate can be used immediately or prepared for storage. The conjugates are preferably stored under conditions offering the greatest stability. Although, such conditions vary for different conjugates, optimum stability is usually achieved by dehydration, and preferably cooling to about $-20°$ C. or less. Conjugates can also be stored hydrated in physiological buffers, at about 4° C., with the addition of an antimicrobial preservative. Suitable buffers include but are not limited to PBS, TBS, BBS, or non-saline buffers which prove effective. Typically, merthiolate (thimerosol) or sodium azide is added at 0.01 to 0.05% to retard microbial growth. Azides should not be used when conjugates are stored in metal containers.

The conjugate is then loaded into a vessel to be used for incubation with a source of IgG, fragments of an IgG, or combinations thereof. Chromatography columns are the preferred incubation vessel. These can be constructed from glass, plastics, or metals, depending on the desired volume and pressure constraints. A wide range of chromatography columns are commercially available for this purpose. The volume of conjugate loaded into the vessel varies according to the dimensions of the vessel, and the quantity of IgG, fragments of an IgG, or combinations thereof, expected to be purified. Optimally, this volume corresponds to the binding capacity of the GB1 polypeptide conjugate, which is determined experimentally for each conjugate preparation. A value of about 1–20 mg per ml of conjugate is generally preferred.

After loading into a vessel, the conjugate may be equilibrated with a buffer compatible with the interaction between the GB1 polypeptide conjugate and an IgG, a fragment of an IgG, or combinations thereof interaction. Suitable buffers include those described above for conjugate storage, except that no preservative would be added. Once equilibrated, a sample containing IgG, a fragment of an IgG, or combinations thereof, is added to the vessel. Optimally, a volume of sample sufficient to completely wet the conjugate is added. This usually represents about 0.3–0.5 volumes of conjugate. Optionally, the sample containing IgG, fragments of an IgG, or combinations thereof is mammalian serum. If not, the sample is preferably a solution in the buffer used to equilibrate the column.

The column and the sample are incubated at room temperature for about 15–60 minutes, then washed thoroughly with equilibration buffer. Buffer passing through the column is monitored for macromolecule content until such content is negligible. This is usually accomplished by measuring the absorbance (280 nm) of the buffer until it returns to the baseline value of the buffer. Buffer fractions can be collected, in that in accordance with one embodiment of the present invention, Fc fragments which are substantially not bound by the GB1 polypeptide are isolated.

After washing, IgG's, fragments of an IgG, or combinations thereof, retained within the matrix are eluted by the addition of an agent which dissociates the IgG's, fragment of an IgG, or combinations thereof from the GB1 polypeptide conjugate. Examples of two of these agents are sodium dodecylsulfate (SDS) ranging in concentration from 0.1–2%, and CCS buffer comprised of 0.02M sodium cacodylate, 0.010M calcium carbonate, and 0.2M sucrose, pH 7.2, containing 0.1–1 unit of neuraminidase.

Up to 90% or greater of the IgG, fragments of an IgG, or combinations thereof is dissociated with SDS. Further dissociation of minute quantities of IgG, fragments of an IgG, or combinations thereof are observed with the latter treatment.

Additional reagents suitable for the elution of IgG's or fragments thereof antibodies may also be employed. These include but are not limited to agents which alter the pH, salt concentration, or hydrophobic interactions affecting the GB1 interaction with IgG's or fragments thereof.

Once eluted, the IgG, fragments of an IgG, or combinations thereof are dialysed thoroughly against a volatile aqueous solvent, which may include solutions of 0.010 to 0.2M ammonium bicarbonate, or ammonium acetate, or distilled water, and then dried in a vacuum evaporator. The dried antibodies is preferably desiccated and stored at about 4° C. Freezing of the IgG, fragments of an IgG, or combinations thereof antibodies should be avoided. Alternatively, the IgG, fragments of an IgG, or combinations thereof can be dialysed into a suitable physiological buffer (see above), concentrated in a vacuum concentrator, and stored in the buffer, supplemented with an antimicrobial agent, as described above.

In accordance with the present invention, a method for purifying Fc fragments of IgG's by affinity chromatography is disclosed. The method comprising the steps of: (a) contacting a sample comprising IgG Fc and at least one of IgG Fab or F(ab')$_2$ fragments with a GB1 polypeptide of the present invention immobilized to a solid phase support to immobilize the IgG Fab or F(ab')$_2$ fragments to the solid phase support; and (b) collecting the IgG Fc fragments remaining in the sample.

Optionally, the method can further comprise the step of washing the solid phase support with a buffer of pH 5 to 8 to give an eluate comprising Fc fragments. Examples of buffers having pH 5 to 8 include, but are not limited to acetate, phosphate, Tris, borate, and bicarbonate.

The Fab or F(ab')$_2$ fragments bound to the immobilized GB1 domain polypeptide may then be recovered by washing the solid phase support with a suitable buffer, such as a buffer of about pH 5 to about pH 8 or a buffer of about pH 3.5 to about pH 2.4. Examples of buffers having pH 5 to 8 include, but are not limited to, acetate, phosphate, Tris, borate, and bicarbonate. Examples of buffers having pH 3.5 to 2.4 include, but are not limited to, acetate, citrate, and glycine.

Thus, in accordance with the present invention, a method for purifying Fab and F(ab')$_2$ fragments of IgG's by affinity chromatography is also disclosed. The method comprising the steps of: (a) contacting a sample comprising IgG Fc and Fab fragments with a GB1 polypeptide of the present invention immobilized to a solid phase support to immobilize the IgG Fab fragments to the solid phase support; (b) collecting the IgG Fc fragment remaining in the sample; and (c) eluting the IgG Fab fragments from the solid phase support to give purified IgG Fab fragments in the eluate. Similar steps are performed with respect to F(ab')$_2$ fragments.

Elution of Fab or F(ab')$_2$ fragments may be accomplished using art recognized techniques, such as pH gradients. For example, it is recognized that protein A binds the Fc portion of IgG antibodies across many mammalian species and may be used to purify IgGs from a complex solution, cells coded with IgG, or Fc fragments of IgG away from Fab fragments. The protocol is to flow the IgG over a protein A-sepharose resin in a 20mM sodium phosphate buffer (pH 7.0) and to continue washing this buffer to remove non-specific binding. The elution is performed with 20mM sodium citrate (pH 4.0). Other acceptable elution techniques are described by Jungpauer, A. et al. (1989) *Journal of Chromatography* 46:257.

J. Preferred Substances for Use in Purification and Detection Methods

Substances suitable for covalent or non-covalent coupling to GB1 polypeptides include, but are not limited to, enzymes such as horseradish peroxidase, alkaline phosphatase, acid phosphatase, and luciferase; radioisotopes such as $^{125}$I, $^{35}$S, $^{14}$C, and $^{3}$H; insoluble beads such as latex, agarose, polyacrylamide, and magnetic particles; solid matrices such as silica, and polystyrene; and colloidal metals such as gold. Conjugation protocols are conventionally standardized for each type of conjugate.

A variety of suitable vessels for incubation mixtures containing antibodies and antibody-binding proteins and polypeptides are available commercially. These include, but are not limited to multiple sample vessels such as microtiter plates and other tissue culture plasticware; vessels for western blot analysis such as staining dishes, slot dishes, and plastic bags; materials for immunofluorescence such as microscope slides, cover slips, and sterile plasticware; chromatography materials such as disposable chromatography columns, syringes, high performance and fast performance chromatography columns; vessels for incubating reagents in suspension such as test tubes, micro centrifuge tubes, beakers, and flasks; and materials for electron microscopic sample incubation such as Parlodion or Formvar-coated electron microscope grids, and Parafilm.

Components preferred for the binding reaction between GB1 polypeptides and IgG's, fragments of an IgG, or combinations thereof would include the components described above; a physiological buffer compatible with the binding reaction such as PBS, TBS or others listed above, or any other buffer which might show applicability through further routine experimentation; and a system for environmental temperature control capable of maintaining the samples at temperatures ranging from 0°–37° C.

Components preferred for the detection and/or visualization of complexes between the GB1 polypeptides of the present invention and an IgG, a fragment of an IgG, or combinations thereof, may include but are not limited to the following: reagents for chromogenic detection of enzyme conjugates such as enzyme substrates, chromogenic dyes, and appropriate reaction buffers, a mechanized colorimeter compatible with the reaction vessel is advantageous for assays on numerous samples; materials for detection of radiolabeled complexes such as gamma or scintillation counters, X-ray film, and autoradiography cassettes; components for fluorescent and illuminescent detection such as fluorescent microscopes and ultraviolet light sources, fluorescence activated cell sorter or flow cytometer, and film; and materials for IEM such as buffers, metallic stains, and an electron microscope with photographic capabilities.

Components preferred for the retention of IgG's, fragments of an IgG, or combinations thereof, onto an insoluble matrix may include, but are not limited to, insoluble conjugates of the GB1 polypeptides of the present invention as listed above.

Components for the recovery of IgG's, fragments of an IgG, or combinations thereof, eluted from a complex between a GB1 polypeptide of the present invention and IgG's, fragments of an IgG, or combinations thereof, may include but are not limited to: materials for chromatographic purification systems such as appropriate elution buffers, an ultraviolet absorbance detector, a fraction collector, and containers or tubes for the collection of eluted material; components for the recovery of IgG's, fragments of an IgG, or combinations thereof, from suspended incubation mixtures would include a dissociation buffer, centrifuge, and container for collecting centrifugal supernatants.

Components preferred for the transfer, dehydration, or concentration of purified IgG's, fragments of an IgG, or combinations thereof, may require but are not limited to the following: a dialysis system including dialysis membrane, a volatile buffer or solvent desired for maintenance of the antibodies such as those listed above, and a vessel in which to dialyse the eluate; a vacuum concentrator or vacuum evaporator to remove undesired quantities of solvent, containers to be appropriate for storing resulting volumes of antibody preparations, and antimicrobial preservative for maintenance of antibody solutions (see above).

By the term "solid phase support" it is intended any support capable of immobilizing a GB1 domain polypeptide of the invention, either covalently, or by adsorption. Solid phase supports which may be used for immobilizing the GB1 domain polypeptide of the invention include, but are not limited to, polymers having hydroxyl groups, either free or in esterified form, such as agarose, cellulose, including cellulose esters such as cellulose nitrate, diazocellulose, cellulose acetate, cellulose propionate, and the like, and acrylamide polymers and copolymers, such as polyacrylamide and acrylamide, microtitre plates, glass, polystyrene, polypropylene, polyethylene, dextran, nylon, agar, starch, or the chemically active membrane having a large surface area comprising a hydrophobic, microporous, skinless, polyamide membrane which is chemically bound to a residue of an activating agent which is capable of immobilizing the GB1 domain polypeptide of the invention. See Deaen et al. (1987) U.S. Pat. No. 4,693,985, herein incorporated by reference.

The GB1 domain polypeptide may be immobilized to the solid phase support according to methods known to those of ordinary skill in the art for protein immobilization. For example, the GB1 domain polypeptide may be coated or bonded, either covalently or by adsorption, to the solid phase. Methods for immobilizing proteins to solid phase supports are taught, for example, in U.S. Pat. Nos. 3,652, 761, 3,879,262, 3,986,217, and 4,693,985, the contents of each of which herein incorporated by reference. Preferably, the GB1 domain polypeptides are immobilized to tresyl activated or cyanogen bromide activated agarose.

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

MATERIALS AND METHODS USED IN THE EXAMPLES

Mutagenesis. The construction of the B1 domain construct (Q32C) was performed as reported by Sloan, D. J. and Hellinga, H. W. (1998) *Prot Eng* 11:819–823. All mutations in this study were constructed in that background by PCR mutagenesis as described by Ho, S. N. et al. (1989) *Gene* 77:55–59). A C-terminal oligo-histidine (His,) affinity tag was used to allow the purification of the mutant proteins by immobilized metal affinity chromatography as described by Hochuli, E. et al. (1988) *Bio/Technology* 6:1321–1325. The recombinant genes were flanked by EcoRl sites that allowed facile cloning into either the pKK223-3 vector for protein expression or the M13 construct for phage display using gIII fusions.

Protein Expression and Purification. The expression and purification of mutant B1 domains was performed as described by Sloan, D. J. and Hellinca, H. W. (1998) *Prot. Eng.* 11:819–823. Briefly, the B1 domain proteins were expressed in the prokaryotic expression vector pKK223-3 (GenBank Accession Number M77749). Pkk223-3 is sold by Amersham-Pharmacia, Uppsala, Sweden. Protein expression is controlled by the Tac promoter. pKK223-3 is grown in the bacterial (*E. coli*) strain XL1-Blue (purchased from Stratagene, La Jolla, Calif.) which expresses the lac repressor allowing for inducible production of the B1 domain proteins. This vector is also described in more detail by Brosius, J. et al. (1981) *Plasmid* 6:112–118 and Brosius, J. et al. (1981) *J. Mol. Biol.* 148:107–127. A typical expression experiment produced 15 milligrams of pure mutant protein from 1 liter of culture.

Fluorophore coupling and iodoacetamide blocking. All of the above mutations were constructed into the Q32C background to allow site-specific covalent coupling with acrylodan for fluorescent binding assays as described by Sloan, D. J. and Hellinca, H. W. (1998) *Prot. Eng.* 11:819–823. In competitive binding experiments between fluorescently labeled wild-type B1 and unlabeled mutants, the free thiol in the mutant protein was blocked by reaction with iodoacetamide.

Binding of B1 mutants to human IgG Fc fragment. The binding constants for each of the alanine mutants were measured as an increase in fluorescence by direct titration of Fc fragment of human IgG (ICN Biomedicals, Costa Mesa, Calif.) into a solution containing 250nM acrylodan-conjugated B1 domain mutant in 20 mM $KPO_4$ (pH 6.0) at 25° C. (excitation 392 nm; emission 500 nm; slit widths of 4 and 16 nm respectively). After each addition of protein, the solution was allowed to equilibrate for 30 seconds before the final fluorescence value was recorded.

Each titration comprised 20 points and was performed in triplicate. The data were fit to a binding isotherm that described a single binding site and takes into account all of the species present (Segel, I. H. (1975) *Enzyme Kinetics*, John Wiley & Sons, New York, N.Y.):

$$F = F_0 + (F_{max} - F_0) \frac{([B1]_t + [hFc]_t + Kd) - \sqrt{([B1]_t + [hFc]_t + Kd)^2 - 4[B1]_t[hFc]_t}}{2[B1]_t}$$

where F is the measured fluorescence with $F_O$ and $F_{max}$ representing the initial and final values, respectively. $[B1]_t$ and $[hFc]_t$ are the concentrations of B1 and hFc respectively, and the $K_d$ is the disassociation constant. This equation is referred to herein as "Equation 1".

The binding constants of weak binders (greater than 50-fold increases in $K_d$) were measured in a competition assay with a pre-formed complex (250 nM) of wild type Q32C construct conjugated to acrylodan and hFc. Binding constants were determined by measuring the decrease in fluorescence of the complex by the addition of iodoacetamide blocked mutant B1 domains. From these competition binding curves the $K_d$ for each of the mutant B1 domains was calculated from the binding isotherm (Fierke, C. A. et al. (1991) *Biochemistry* 30:11054–11063):

$$F = \frac{F_0}{1 + \left(\frac{K_{DWT}}{[B1_{wt}]}\right) \times \left(1 + \frac{[B1_{mut}]}{K_{Dmut}}\right)} + F_f$$

where F is the measured fluorescence with $F_o$ and $F_f$ representing the initial and final values respectively. $[B1_{wt}]$ and $[B1mut]$ are the concentrations of B1 wild type and mutant respectively, and the $K_d$ is the disassociation constant of the mutant or wild type. This Equation is referred to herein as "Equation 2".

Phage Display. A gly-gly-gly-ser-gly-gly-gly-ser linker was inserted into the NotI site of pCANTAB5 (Pharmacia, Bridgewater, N.J.) to reduce the interactions between the displayed protein and PIII in accordance with techniques disclosed by Smith, G. P. and Scott, J. K. (1993) *Methods Enzymol.* 217:228–257. The resulting gIII gene fusion was sub-cloned from pCANTAB5 into the multiple cloning site of M13mpl8 (Messing, J. (1991) *Gene* 100:3–12). A unique NheI site was introduced into the gIII fusion by site-directed mutagenesis as described by Kunkel, T. A. (1985) *Proc. Natl. Acad. Sci. USA* 82:488492) into which the B1 gene was cloned. Alanine mutations were constructed directly into this vector.

Biopanning as described by Smith, G. P. and Scott, J. K. (1993) *Methods Enzymol.* 217:228–257 was used to determine the Fab-binding properties of the fusion constructs, using 100 ng biotinylated IgG, $5 \times 10^9$ pfu of each B1 bacteriophage, high protein binding ELISA wells (Greiner, Kremsmunster, Austria), and 2% non-fat dry milk blocking solution. Binding between mutant B1 and IgG was detected by anti-M13 antibody-HRP conjugate (Pharmacia, Bridgewater, N.J.; manufacturers protocol). Control experiments in which the Fab fragment was left out were done in parallel to rule out non-specific binding.

Table 3 presents the nucleic acid and peptide sequences of the naturally occurring or native GB1 polypeptide including a methionine residue at amino acid residue −1 which was incorporated through recombinant DNA techniques to facilitate expression of the polypeptide in the expression vector system disclosed herein. Table 4 summarizes the Examples, which comprises the mutant GB1 polypeptides of the present invention.

Figure 1C:
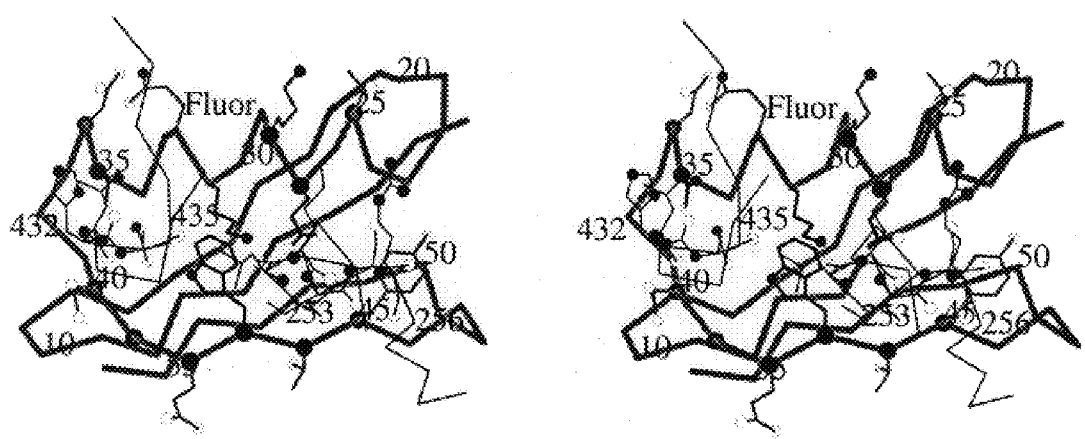
FIG. 1C depicts a stereopair showing details of the interaction between the B1 domain (heavy lines) and the $C_\gamma 2$-$C_\gamma 3$ region of the Fc fragment (light lines).

4). Single alanine mutants of each of these residues were constructed. These are located in the alpha helix, the third β strand, and the loop between this helix and strand (FIG. 1).

Binding studies. The interaction of the mutant B1 domain with the hFc was measured using a fluorescence method described by Sloan, D. J. and Hellinga, H. W. (1998) *Prot.*

TABLE 3

Nucleic Acid and Peptide Sequences of Native B1 Domain of Protein G
(SEQ ID No:1 and SEQ ID NO:2)

```
ATG ACT ACT TAC AAA TTA ATC CTT AAT GGT AAA ACA TTG AAA GGC GAA ACA
MET THR THR TYR LYS LEU ILE LEU ASN GLY LYS THR LEU LYS GLY GLU THR

ACT ACT GAA GCT GTT GAT GCT GCT ACT GCA GAA AAA GTC TTC AAA CAA TAC
THR THR GLU ALA VAL ASP ALA ALA THR ALA GLU LYS VAL PHE LYS GLN TYR

GCT AAC GAC AAC GGT GTT GAC GGT GAA TGG ACT TAC GAC GAT GCG ACT AAG
ALA ASN ASP ASN GLY VAL ASP GLY GLU TRP THR TYR ASP ASP ALA THR LYS

ACC TTT ACA GTT ACT GAA CAT CAC CAT CAT CAC TAA GCT TGA
THR PHE THR VAL THR GLU HIS HIS HIS HIS HIS OCH ALA OPA
```

Met is residue −1 and the start site of translation in the expression vector system disclosed herein.
Underlined residues are the polyhistidine tag used for purification in immobilized metal affinity chromatography.
*Italicized* are two stop codons used to terminate translation.
Shown in bold is the crucial residue glutamate 27 which when mutated to alanine (GCG) or to any other amino acid abolishes binding to the Fc fragment of IgG while retaining binding to Fab fragments.
Shown in *italics and underlining* are other residues described in Table 3 which when mutated to alanine (GCG) substantially abolish binding to the Fc fragment of IgG while retaining binding to Fab fragments. In accordance with the present invention other amino acids can be substituted for these residues, including for example, valine, leucine and isoleucine. Codons for such substitutions can be selected from Table 2.

TABLE 4

| Example | Mutant | $K_d{}^a$ (mM) | $DDG^b$ (kcal/mole) | H-bonds$^c$ | $f_{SASA}{}^d$ | SEQ ID NO |
|---|---|---|---|---|---|---|
| 1 | Q32C$^e$ | 0.24 | 0 | 1 | 0.53 | 3 |
| 2 | T25A | 0.36 | 0.24 | 0 | 0.6 | 4 |
| 3 | E27A | >1000$^f$ | >4.9$^f$ | 3 | 1 | 6 |
| 4 | K28A | 2.0 | 1.3 | 1 | 0.95 | 8 |
| 5 | K31A | 85 | 3.5 | 0 | 0.94 | 10 |
| 6 | N35A | 13 | 2.4 | 2 | 0.79 | 12 |
| 7 | D40A | 0.38 | 0.3 | 0 | 0.40 | 13 |
| 8 | E42A | 0.46 | 0.4 | 1 | 0.30 | 14 |
| 9 | W43A | 140 | 3.8 | 1 | 0.89 | 16 |
| 10 | T44/Y45A | 6.5 | 2.0 | 0 | 0.43 | 18 |

$^a K_d$ calculated from Equation 1.
$^b DDG = -RT\ln(K_d \text{ wild type}/K_d \text{ mutant}); T = 298K$.
$^c$Number of hydrogen bonds formed by the native, non-mutated residue and the Fc as determined by inspection of the crystal structure of FIG. 1.
$^d f_{SASA}$ is fractional change in solvent accessible surface area: $f_{SASA}$= SASA (complex)/ SASA (free)
$^e$The wild-type construct relative to which all measurements are made.
$^f$Binding is too weak to be quantified.

RESULTS OF EXAMPLES

Mutagenesis of the Fc-binding site on the B1 domain. The X-ray structure of the complex between the B1 and a human IgG Fc fragment (hFc) depicted schematically in FIG. 1 and as described by Sauer-Eriksson, A. E. et al. (1995) *Structure* 3:265–278 was used to identify the residues located in the interface between these two proteins. The static solvent-accessible surface (Richards, F. M. (1977) *Annual Review of Biophysics and Bioengineering* 6:151–176) was calculated for the B1 domain in the presence and absence of the hFc fragment. Eleven residues showed a significant decrease in solvent accessibility in the structure of the complex (Table

Figure 2A:
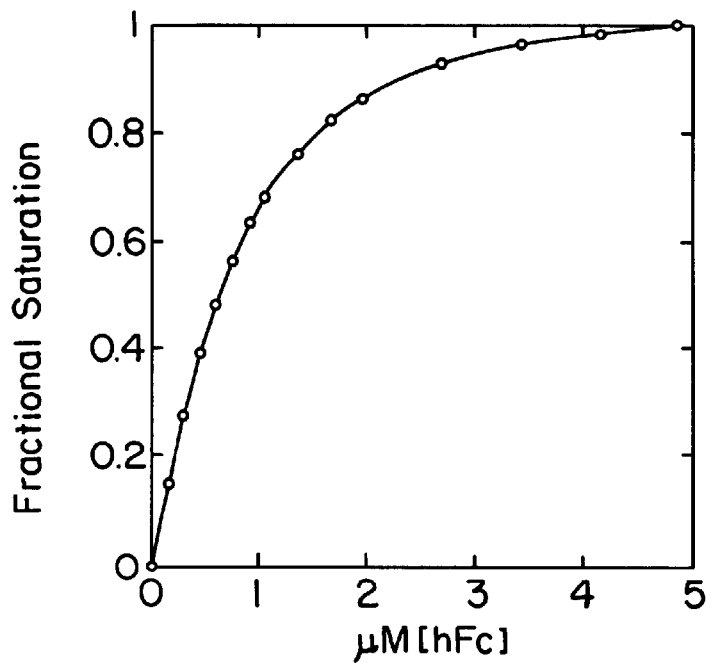
FIG. 2A is a line graph depicting titration of the unlabeled Fc fragment into a solution of 250 nM of the T25A mutant B1 domain. The data was fit to Equation 1. Experimental Error bars are smaller than symbols on graph.

*Eng.* 11:819–823, which relies on the attachment of an environmentally sensitive fluorophore placed at the rim of the binding site in a location such that its fluorescence changes upon formation of the complex by virtue of alterations in conformational degrees of freedom and solvent accessibility, without adversely affecting the binding constant. Binding constants for hFc were determined in a direct titration experiment in which purified hFc was added to a solution of a Q32C B1 mutant to which the fluorophore acrylodan was covalently coupled at position 32C (FIG. 2A). The binding constants for all the B1 mutants were determined in the Q32C background (Table 4).

Figure 2B:
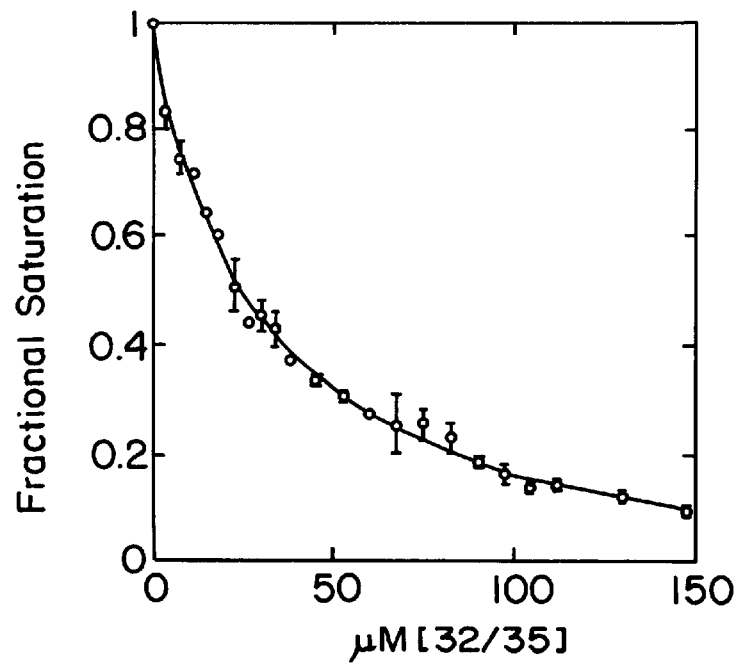
FIG. 2B is a line graph depicting determination of the free energy of binding of a weakly binding B1 mutant, N35A, by a competition experiment in which unlabeled mutant protein is titrated into a 250 nM preformed complex of fluorescent wild-type B1 and human Fc. The data was fit to Equation 1.

For those mutants whose $K_d$ showed a greater than fifty-fold increase, the binding constants were determined in a competition experiment in which a complex was preformed between fluorescently labeled wild-type B1 (Q32C) and hFc, which was then titrated with an unlabeled, mutant B1 domain whose free cysteine at position 32 had been blocked with iodoacetamide (FIG. 2B). This approach was used to avoid having to use large quantities of pure hFc.

In order to verify that large decreases in the binding constants were not due to loss of structure, we took advantage of the fact that B1 has a separate binding site for the Fab fragment, which does not overlap with the Fc binding site. Fab binding was determined semi-quantitatively by phage display in M13 as described by Smith, G. P. and Scott, J. K. (1993) *Methods Enzymol.* 217: 228–257 using a genetic fusion between gene III and B1, expressed as a second copy in the phage genome, as described by Armstrong, N. et al. (1996) in *Phage display of peptides and proteins* (Kay, B. K., Winter, J., & McCafferty, J., Eds.) pp. 35–53, Academic Press, Inc., San Diego, Calif., in order to obtain uni-valent rather than poly-valent display of the B1 domain. See also McConnell, S. J. (1994) *Gene* 151:115–118. In all cases, the mutants constructed in the Fc-binding site retained the ability to bind Fab, indicating that there was no significant loss in overall structure.

The results show that five out of the ten residues in the binding site had a significant effect on hFc binding ($K_d$ increased at least ten-fold), whereas the other five showed little or no effect (less than two-fold change in $K_d$). A single mutant, E27A, virtually abolished binding (>4000-fold increase in $K_d$). The five residues that most affected binding form a contiguous patch on the surface of B1, surrounded by a ring of the other residues (FIG. 1).

DISCUSSION OF EXAMPLES

The experiments described herein report the energetic contributions of the residues forming the binding site between the B1 domain of protein G and human IgG Fc fragment. The X-ray structure of a complex between the B1 domain and hFc show that about thirteen residues on the surface of B1 are directly involved in the binding site as defined by a change in their solvent-accessible area upon complex formation. Three of these residues are alanines and glycine scanning mutagenesis was not performed to determine the energetic contribution of these residues. Alanine mutations of only about half of the ten mutated residues significantly affect the binding free energy (at least ten-fold increase in $K_d$. Within these five residues the effect of binding varies sharply, ranging from 10-fold to more than 4000-fold increases in $K_d$, indicating that the determinants contributing to the free energy of binding are highly localized. The localization of binding energy to such "hot-spots" has also been observed in other heterodimeric interfaces (Bogan A. A. and Thorn K. S. (1998) *J. Mol. Biol.* 280:1–9); (Wells, J. A. (1991) *Methods Enzymol.* 202:390–411).

The binding hot-spots on the surface of the B1 domain are associated with clear structural motifs. The binding site is formed by two "knobs-into-holes" interactions. E27 of the B1 domain fits into a hole formed by I253 and S254 on the surface of the Fc fragment, where the carboxylate forms hydrogen bonds with the backbone amides of these residues as well as the $O_\gamma$ of S254. Mutation of this charged knob on the surface of the B1 domain virtually completely abolishes binding. The carboxylate of E27 is held in position by a hydrogen bond from the amino group of K31, the neighboring residue, on the surface of B1. Removal of this interaction in the K31A mutant significantly decreases affinity (350-fold increase in $K_d$). The second knob-into-hole interaction is formed by the protrusion of N434 from the surface of the Fc into a hole in B1 bordered by N35, D36, D40, E42 and W43. The indole nitrogen of W43 forms a hydrogen bond with N434. Of all the bordering residues forming the hole on B1, the W43A mutant has the most profound effect on the interaction (580-fold increase in $K_d$), presumably as a direct consequence of this interaction. Of the other residues, only N35A significantly affects binding (50-fold increase in $K_d$). Interestingly, it makes a hydrogen bond with H433 on the hFc.

These results quantify the contribution of the individual residues identified in the high-resolution structure of the B1-hFc complex (Sauer-Eriksson, A. E. et al. (1995) *Structure* 3:265–278). It was noted in the description of this structure that all of these residues are involved in contacts between the two proteins. From this study it is clear, however, that only a small subset make significant contribution to the free energy of binding, illustrating the importance of combining structural information with thermodynamic data. It should be emphasized that in an alanine-scanning mutagenesis experiment side-chains are deleted. Lack of a large effect upon loss of an interaction does not imply that the choice of a particular amino acid is unimportant, since replacement with residues which result in incorrect steric packing or charge complementarity may adversely affect proper formation of the interface. Furthermore, an alanine scanning experiment does not address the issue of main-chain interactions. Two B1 domain residues potentially form main chain interactions with hFc residues, those being the nitrogen of G41 and the carbonyl oxygen of V39 (Sauer-Eriksson, A. E. et al. (1995) *Structure* 3:265–278).

The four critical binding residues within the B1 domain are glutamate, tryptophan, lysine, and asparagine. Tryptophan is frequently found within interfaces, whereas lysine and asparagine are not normally enriched, and glutamate is under represented in heterodimer interfaces. See Bogan A. A. and Thorn K. S. (1998) *J. Mol. Biol.* 280:1–9. It has been suggested that hot spots located in planar interfaces need to be surrounded by a ring of residues that exclude bulk solvent (the O-ring hypothesis), aiding in the formation of polar hydrogen bonds (Bogan A. A. and Thorn K. S. (1998) *J. Mol. Biol.* 280:1–9). The polar knobs-into-holes binding motif observed in the B1 domain provides another mechanism to form buried, polar hydrogen bonds.

The existence of a well-defined hot-spot suggests that it may be possible to develop a low-molecular weight reagent that could disrupt this interface. Such a reagent could have applications in immunochemistry as well in treatment of streptococcal infections by potentially unmasking bacteria cloaked in a coat of antibodies.

REFERENCES

The references listed below as well as all references cited in the specification are incorporated herein by reference to the extent that they supplement, explain, provide a background for or teach methodology, techniques and/or compositions employed herein.

Adelman et al. (1983) *DNA* 2:183.
Amante et al. *J. Immunol. Meth.*, 1:289 (1972)
Argos, P. (1988) *Prot Eng* 2: 101–113.
Armstrong, N. et al. (1996) in *Phage display of peptides and proteins* (Kay, B. K., Winter, J., & McCafferty, J., Eds.) pp 35–53, Academic Press, Inc., San Diego, Calif.

Ausubel et al. (1992) *Current Protocols in Molecular Biology*, John Wylie & Sons, New York, N.Y.
Blakeslee et al. *J. Immunol. Meth.* 13:320 (1977)
Bodanszky et al. (1976) "Peptide Synthesis", John Wiley & Sons, Second Edition, New York, N.Y.
Bogan A. A. and Thorn K. S. (1998) *J. Mol. Biol.* 280:1–9.
Boyle, M. D. P. (1990) *Bacterial Immunoglobulin-binding proteins*, Academic Press, San Diego, Calif.
Brosius, J. et al. (1981) *J. Mol Biol.* 148:107–127.
Brosius, J. et al. (1981) *Plasmid* 6:112–118.
Carlsson et al. (1978) *Biochem. J.* 173:723
Crea et al. (1978) *Proc. Natl. Acad. Sci. USA*, 75:5765.
Crick, F. H. C. (1952) Nature 170: 882–883.
Crick, F. H. C. (1953) Acta Crystallographica 6: 689–697.
Davies, D. R. and Cohen, G. H. (1996) *Proc. Natl. Acad. Sci. USA* 93:7–12.
Deisenhofer, J. (1981) *Biochemistry* 20:2361–2370.
Derrick, J. P. and Wigley, D. B. (1992) Nature 359: 752–754.
Eichenlaub et al. (1979) *J. Bacteriol.* 138:559–566.
Fields et al. (1990) *Int. J. Peptide Protein Res.* 35:161–214.
Fierke, C. A. et al. (1991) *Biochemistry* 30: 11054–11063.
Frick, I-M. et al. (1992) *Proc. Natl. Acad. Sci. USA* 89:8532–8536.
Goward, C. R. et al. (1993) *Trends Biochem. Sci.* 18:136–140.
Gribskov et al. (1986) *Nucl. Acids. Res.* 14:6745.
Gronenborn, A. M. and Clore, G. M. (1993) *J. Mol. Biol.* 233:331–335.
Harlow et al. (1988) *Antibodies: a laboratory manual*, Cold Spring Harbor Laboratory, Cold Spring Harbor, N.Y.
Ho, S. N. et al. (1989) *Gene* 77:55–59.
Hochuli, E. et al. (1988) *Bio/Technology* 6:1321–1325.
Horisberger et al. *Histochem.* 82:219 (1985)
Ishikawa et al. (1978) *Scand. J. Immunol.* 8:43
Jones, S. and Thornton, J. M. (1996) *Proc. Natl. Acad. Sci. USA* 93:13–20.
Jungpauer, A. et al. (1989) *Journal of Chromotography* 46:257.
Kato, K. et al. (1995) *Structure* 3:79–85.
Kunkel, T. A. (1985) *Proc. Natl. Acad. Sci. USA* 82:488–492.
LeConte, L. et al. (1999) *J. Mol. Biol.* 285:2177–2198.
McConnell, S. J. (1994) *Gene* 151:115–118.
McKinney et al. (1966) *Anal. Biochem.* 14:421
McOmie (1973) *Protective Groups in Organic Chemistry*, Plenum Press, New York, N.Y.
Meienhofer (1983) *Hormonal Proteins and Peptides*, Vol. 2, p. 46, Academic Press, New York, N.Y.
Merrifield (1969) *Adv Enzymol* 32:221–96.
Messing, J. (1991) *Gene* 100:3–12.
Messing et al. (1981) *Third Cleveland Symposium on Macromolecules and Recombinant DNA*, Editor A. Walton, (Elsevier, Amsterdam).
Needleman et al. (1970) *J. MoL Biol.* 48:443.
O'Sullivan et al. (1978) *FEBS Letters* 95:311
Richards, F. M. (1977) *Annual Review of Biophysics and Bioengineering* 6: 151–176.
Robinson et al. (1984) *Infect. Immun.* 46:361–366.
Sambrook et al. (1989) *Molecular Cloning: A Laboratory Manual* (Cold Spring Harbor Laboratory Press, Cold Spring Harbor, N.Y.
Sauer-Eriksson, A. E. et al. (1995) *Structure* 3:265–278.
Schroder et al. (1965) *"The Peptides"*, Vol.1, Academic Press, New York, N.Y.
Schwartz et al., eds. (1979) *Atlas of Protein Sequence and Structure, National Biomedical Research Foundation*, pp. 357–358.
Segel, l. H. (1975) Enzyme Kinetics, John Wiley & Sons, New York, N.Y.
Sloan, D. J. and Hellinga, H. W. (1998) *Prot. Eng.* 11: 819–823.
Smith, G. P. and Scott, J. K. (1993) *Methods Enzymol.* 217: 228–257.
Smith et al. (1981) *Adv. Appl. Math.* 2:482.
Stahl, S. et al. (1993) *Current Opinion in Immunology* 5: 272–277.
Steward et al. (1969) *"Solid Phase Peptide Synthesis"*, W. H. Freeman Co., San Francisco, Calif.
Stites, W. E. (1997) *Chem. Rev.* 97:1233–1250.
Stone, G. C. et al. (1989) *J. Immunol.* 143:565–570.
Tsunogae, Y. et al. (1986) *J. Biochem.* 100:1637–46.
U.S. Pat. No. 3,879,262
U.S. Pat. No. 4,554,101
U.S. Pat. No. 3,652,761
U.S. Pat. No. 3,850,798
U.S. Pat. No. 3,986,217
U.S. Pat. No. 4,693,985
U.S. Pat. No. 4,244,946
U.S. Pat. No. 4,977,247
Wells, J. A. and deVos, A. M. (1996) *Ann Rev Biochem* 65: 609–634.
Wells, J. A. (1991) *METHODS Enzymol* 202: 390–411.
Wetmur & Davidson (1968) *J. Mol. Biol.* 31:349–370.
Zimmer et al. (1993) *Peptides* 1992, pp.393–394, ESCOM Science Publishers, B. V.

It will be understood that various details of the invention may be changed without departing from the scope of the invention. Furthermore, the foregoing description is for the purpose of illustration only, and not for the purpose of limitation—the invention being defined by the claims.

What is claimed is:

1. An isolated B1 domain of protein G (GB1) polypeptide which maintains binding activity for an antigen binding (Fab) fragment of an imuunoglobulinG (IgG) but exhibits substantially no binding activity for a readily crystallized (Fc) fragment of an IgG, wherein the substantially no binding activity for a Fc fragment of an IgG is a dissociation constant for a Fc fragment of an IgG of greater than about 2 mM.

2. An isolated B1 domain of protein G (GB1) polypeptide which maintains binding activity for a Fab fragment of an IgG but exhibits substantially no binding activity for a Fc fragment of an IgG, wherein the substantially no binding activity for a Fc fragment of an IgG is a dissociation constant for a Fc fragment of an IgG of greater than about 2 mM, wherein said B1 domain further comprises a mutated "knobs-into-holes" binding site for a Fc fragment of an IgG wherein the "knobs-into holes" binding site comprises a knob from the GB1 domain polypeptide that protrudes into a hole on the Fc fragment or a hole on the GB1 domain polypeptide that receives a knob from the Fc fragment, wherein the knob from the GB1 domain polypeptide comprises residues E27 and K31, and the hole on the Fc fragment comprises residues I253 and S254; and wherein the hole on the GB1 domain polypeptide comprises residues N35, D36, D40, E42 and W43, and the knob from the Fc fragment comprises residue N434 of Brookhaven protien database accession number 1fcc.

3. The isolated GB1 domain polypeptide of claim 2, wherein the mutated "knobs-into-holes" binding site for a Fc fragment of an IgG comprises an amino acid substitution.

4. The isolated GB1 domain polypeptide of claim 3, wherein the amino acid substitution comprises a comparatively non-polar amino acid residue in place of a polar amino acid residue.

5. The isolated GB1 domain polypeptide of claim 3, further comprising a mutation at the glutamate 27 residue of a native GB1 domain polypeptide, the mutation comprising an amino acid substitution of the glutamate 27 residue.

6. The isolated GB1 domain polypeptide of claim 5, having an amino acid sequence essentially as set forth in any SEQ ID NO:6, 20, 22 and 24.

7. The isolated GB1 domain polypeptide of claim 3, further comprising a mutation at a lysine 28 residue of a native GB1 domain polypeptide, the mutation comprising an amino acid substitution of the lysine 28 residue.

8. The isolated GB1 domain polypeptide of claim 7, wherein the mutation comprises substitution of the lysine 28 residue with a comparatively non-polar amino acid residue.

9. The isolated GB1 domain polypeptide of claim 8, wherein the non-polar amino acid residue is selected from the group consisting of alanine, valine, leucine and isoleucine.

10. The isolated GB1 domain polypeptide of claim 9, having an amino acid sequence essentially as set forth in SEQ ID NO:8.

11. The isolated GB1 domain polypeptide of claim 3, further comprising a mutation at a lysine 31 residue of a native GB1 domain polypeptide, the mutation comprising an amino acid substitution of the lysine 31 residue.

12. The isolated GB1 domain polypeptide of claim 11, wherein the mutation comprises substitution of the lysine 31 residue with a comparatively non-polar amino acid residue.

13. The isolated GB1 domain polypeptide of claim 12, wherein the non-polar amino acid residue is selected from the group consisting of alanine, valine, leucine and isoleucine.

14. The isolated GB1 domain polypeptide of claim 13, having an amino acid sequence essentially as set forth in SEQ ID NO:10.

15. The isolated GB1 domain polypeptide of claim 3, further comprising a mutation at an asparagine 35 residue of a native GB1 domain polypeptide, the mutation comprising an amino acid substitution of the asparagine 35 residue.

16. The isolated GB1 domain polypeptide of claim 15, wherein the mutation comprises substitution of the asparagine 35 residue with a comparatively non-polar amino acid residue.

17. The isolated GB1 domain polypeptide of claim 16, wherein the non-polar amino acid residue is selected from the group consisting of alanine, valine, leucine and isoleucine.

18. The isolated GB1 domain polypeptide of claim 17, having an amino acid sequence essentially as set forth in SEQ ID NO:12.

19. The isolated GB1 domain polypeptide of claim 3, further comprising a mutation at a tryptophan 43 residue of a native GB1 domain polypeptide, the mutation comprising an amino acid substitution of the tryptophan 43 residue.

20. The isolated GB1 domain polypeptide of claim 19, wherein the mutation comprises substitution of the tryptophan 43 residue with a comparatively non-polar amino acid residue.

21. The isolated GB1 domain polypeptide of claim 20, wherein the non-polar amino acid residue is selected from the group consisting of alanine, valine, leucine and isoleucine.

22. The isolated GB1 domain polypeptide of claim 21, having an amino acid sequence essentially as set forth in SEQ ID NO:16.

23. The isolated GB1 domain polypeptide of claim 3, further comprising mutations at a threonine 35 residue and at a tyrosine 45 residue of a native GB1 domain polypeptide, the mutation comprising an amino acid substitution of the threonine 35 residue and of the tyrosine 45 residue.

24. The isolated GB1 domain polypeptide of claim 23, wherein the mutation comprises substitutions of the threonine 35 residue and the tyrosine 45 residue with a comparatively non-polar amino acid residue.

25. The isolated GB1 domain polypeptide of claim 24, wherein the non-polar amino acid residue is selected from the group consisting of alanine, valine, leucine and isoleucine.

26. The isolated GB1 domain polypeptide of claim 25, having an amino acid sequence essentially as set forth in SEQ ID NO:18.

27. The isolated GB1 domain polypeptide of claim 1, further characterized as immobilized to a solid phase support.

28. The GB1 domain polypeptide of claim 1, wherein the Fab and the Fc fragments are from an IgG from a warm-blooded vertebrate.

29. The GB1 domain polypeptide of claim 28, wherein the Fab and the Fc fragments are from an IgG from a mammal.

30. The GB1 domain polypeptide of claim 29, wherein the mammal is selected from the group consisting of human, mouse, pig, rat, ape, monkey, cat, guinea pig, cow, goat and horse.

\* \* \* \* \*